US008951499B2

(12) United States Patent
Wilbur et al.

(10) Patent No.: US 8,951,499 B2
(45) Date of Patent: Feb. 10, 2015

(54) TRIFUNCTIONAL REAGENT FOR CONJUGATION TO A BIOMOLECULE

(75) Inventors: D. Scott Wilbur, Edmonds, WA (US); Bengt E. B. Sandberg, Hjärup (SE)

(73) Assignees: University of Washington, Seattle, WA (US); Glycorex Transplantation AB, Lund (SE)

( * ) Notice: Subject to any disclaimer, the term of this patent is extended or adjusted under 35 U.S.C. 154(b) by 2386 days.

(21) Appl. No.: 11/516,419

(22) Filed: Sep. 6, 2006

(65) Prior Publication Data

US 2007/0071673 A1    Mar. 29, 2007

Related U.S. Application Data

(63) Continuation of application No. 09/750,280, filed on Dec. 29, 2000, now abandoned, which is a continuation of application No. PCT/SE99/01241, filed on Jul. 7, 1999, and application No. 11/516,419, and a continuation-in-part of application No. 10/261,040, filed on Sep. 30, 2002, now Pat. No. 7,141,676, which is a continuation-in-part of application No. 09/324,267, filed on Jun. 2, 1999, now abandoned, which is a continuation-in-part of application No. 08/798,413, filed on Feb. 7, 1997, now abandoned.

(60) Provisional application No. 60/011,321, filed on Feb. 8, 1996.

(30) Foreign Application Priority Data

Jul. 7, 1998 (WO) ........................ PCT/SE98/01345

(51) Int. Cl.
| | | |
|---|---|---|
| A61K 51/00 | (2006.01) | |
| C07D 235/02 | (2006.01) | |
| C07F 5/00 | (2006.01) | |
| A61K 31/4188 | (2006.01) | |
| A61K 31/765 | (2006.01) | |
| C07D 233/32 | (2006.01) | |
| C07D 495/04 | (2006.01) | |
| C07D 519/00 | (2006.01) | |
| G01N 33/532 | (2006.01) | |
| G01N 33/543 | (2006.01) | |

(52) U.S. Cl.
CPC ........... *A61K 31/4188* (2013.01); *A61K 31/765* (2013.01); *C07D 233/32* (2013.01); *C07D 495/04* (2013.01); *C07D 519/00* (2013.01); *G01N 33/532* (2013.01); *G01N 33/54353* (2013.01)
USPC ....... 424/1.11; 424/1.49; 540/474; 548/304.1; 534/11

(58) Field of Classification Search
None
See application file for complete search history.

(56) References Cited

U.S. PATENT DOCUMENTS

| | | | |
|---|---|---|---|
| 4,877,868 A | | 10/1989 | Reno et al. |
| 5,124,471 A | * | 6/1992 | Gansow et al. ................. 558/17 |
| 5,134,071 A | | 7/1992 | Gaetjens |
| 5,273,743 A | | 12/1993 | Ahlem et al. |
| 5,286,850 A | | 2/1994 | Gansoh et al. |
| 5,310,916 A | | 5/1994 | Jacobson et al. |
| 5,474,772 A | | 12/1995 | Maddock |
| 5,482,698 A | | 1/1996 | Griffiths |
| 5,541,287 A | | 7/1996 | Yau et al. |
| 5,578,287 A | | 11/1996 | Theodore et al. |
| 5,608,060 A | * | 3/1997 | Axworthy et al. ............ 540/474 |
| 5,739,287 A | | 4/1998 | Wilbur et al. |
| 5,840,880 A | | 11/1998 | Morgan et al. |
| 6,083,926 A | | 7/2000 | Morgan et al. |
| 7,141,676 B1 | | 11/2006 | Wilbur et al. |
| 2002/0159994 A1 | | 10/2002 | Sandberg et al. |
| 2004/0052784 A1 | | 3/2004 | Sandberg et al. |
| 2005/0271673 A1 | | 12/2005 | Wilbur et al. |
| 2006/0222588 A1 | | 10/2006 | Sandberg et al. |

FOREIGN PATENT DOCUMENTS

| | | |
|---|---|---|
| AU | B-64268/90 | 3/1991 |
| EP | 0310361 | 4/1989 |
| EP | 0567 514 | 11/1993 |
| EP | 0618192 | 10/1994 |
| WO | WO 89/10140 | 11/1989 |
| WO | WO 91/01749 | 2/1991 |
| WO | WO 9218536 A2 * | 10/1992 |

(Continued)

OTHER PUBLICATIONS

Boring, D.L., et al., "Trifunctional Agents as a Design Strategy . . . ", 1991, Bioconjugate Chem, 2, pp. 77-88.*
Ashwell, G. et al. "The Role of Surface Carbohydrates in the Hepatic Recognition and Transport of Circulating Glycoproteins," (1974) Adv. Enzymol. 41:99-128.
Behr, T et al. "Phase I/II Clinical Radioimmunotherapy with an Iodine-131-Labeled Anti-Cardioembryonic Antigen Murine Monoclonal Antibody IgG," (1997) J. Nucl. Med 38(6):858-870.
Bender, H. et al., "Clinical Aspects of Local and Regional Tumor Therapy with 188Re-RC-160," (1997) Anticanc. Res. 17:1705-1712.

(Continued)

*Primary Examiner* — Michael G Hartley
*Assistant Examiner* — Lance Rider
(74) *Attorney, Agent, or Firm* — Christensen O'Connor Johnson Kindness PLLC

(57) ABSTRACT

A reagent for conjugation to a biomolecule, wherein the reagent is a single molecule with at least three functional parts and has schematic structure (I): a) wherein a trifunctional cross-linking moiety is coupled to b) an affinity ligand via a linker 1, said affinity ligand being capable of binding with another molecule having affinity for said ligand, to c) an effector agent, optionally via a linker 2, said effector agent exerting its effect on cells, tissues and/or humorous molecules in vivo or ex vivo, and to d) a biomolecule reactive moiety, optionally via a linker 3, said moiety being capable of forming a bond between the reagent and the biomolecule.

25 Claims, No Drawings

(56) References Cited

FOREIGN PATENT DOCUMENTS

| WO | WO 93/02105 | 2/1993 |
|---|---|---|
| WO | WO 96/04313 | 2/1996 |
| WO | WO 97/29114 | 8/1997 |
| WO | WO 99/04820 | 2/1999 |
| WO | WO 00/02050 | 1/2000 |
| WO | WO 00/02051 | 1/2000 |
| WO | WO 00/72802 | 12/2000 |

OTHER PUBLICATIONS

Blakey, D.C. et al., "ZD2767, an Improved System for Antibody Directed Enzyme Prodrug Therapy that Results in Tumor Regressions in Colorectal Tumor Xenographs," (1996) Canc. Res. 56:3287-92.
Corbett J., "Clinical Experience with Iodine-123-Iodophenylpentadecanoic Acid," (1994) J. Nucl. Med. 35(4) (Suppl.):32s-37s.
Denardo, GL et al., "Immunoadsorption: an Enhancement Strategy for Radioimmunotherapy," (1993) J. Nucl. Med. 34(6):1020-27.
Denardo, SJ et al., "Yttrium-90/Indium-111-DOTA-Peptide-Chimeric L6: Pharmacokinetics, Dosimetry and Initial Results in Patients with Incurable Breast Cancer," (1997) Anticanc. Res. 17:1735-1744.
Dienhart, DG et al., "Extracorporeal Immunoadsorption of Radiolabeled Monoclonal Antibody: A Method for Reduction of Background Radioactivity and Its Potential Role During the Radioimmunotherapy of Cancer," (1994) Antibody, Immunoconjugates, and Radiopharmaceuticals 7(4):225-252.
Divgi CR et al., "Phase I Radioimmunotherapy Trial with Iodine-131-CC49 in Metastatic Colon Carcinoma," (1995) J. Nucl. Med. 36(4):586-592.
Garkavij, M et al., "Extracorporeal Whole-Blood Immunoadsorption Enhances Radioimmunotargeting of Iodine-125-Labeled BR96—Biotin Monoclonal Antibody," (1997) J. Nucl. Med. 38(6):895-901.
Garkavij, M et al., "Extracorporeal Immunoadsorption from Whole-Blood Based on the Avidin-Biotin Concept Evaluation of a New Method," (1996) Acta Oncologica 35(3):309-312.
Goldenberg, DM et al., "Clinical Studies of Cancer Radioimmunodetection with Carcinoembryonic Antigen Monoclonal Antibody Fragments Labeled with 123I or 99mTC," (1990) Canc. Res. (Suppl.) 50:909s-921s.
Granowska, M. et al., "Radioimmunoscintigraphy with Technetium-99m-labelled monoclonal antibody, SM3, in gynaecological cancer," (1993) Eur. J. Nucl. Med. 20(6):483-89.
Green, NM, "Avidin" (1975) Adv. Prot. Chem. 29:85-132.
Green, NM, "Avidin and Streptavidin," (1990) Methods in Enzymol. 184:51-67.
Hansen, C., "Preliminary Report of an Ongoing Phase I/II Dose Range, Safety and Efficacy Study of Iodine-123 Phenylpentadecanoic Acid for the Identification of Viable Myocardium," (1994) J. Nucl. Med. 35(4) (Suppl.):38s-42s.
Henry, C. et al., "Improved Monoclonal Antibody Tumor/Background Ratios with Exchange Transfusions," (1991) Nucl. Med. Biol. 18(5):565-567.
Houba, P et al., "Improved Characteristics of a Human B-Glucuronidase-Antibody Conjugate after Deglycosylation for Use in Antibody-Directed Enzyme Prodrug Therapy," (1996) Bioconjugate Chem. 7(5):606-611.
Johnson, TK et al., "Radioimmunoadsorption of KC-4G3 Antibody in Peripheral Blood: Implications for Radioimmunotherapy," (1991) Antibody, Immunoconjugates and Radiopharmaceuticals 4(4):885-893.
Klibanov, AL et al., "Blood Clearance of Radiolabeled Antibody: Enhancement by Lactosamination and Treatment with Biotin-Avidin or Anti-Mouse IgG Antibodies," (1998) J. Nucl. Med. 29(12):1951-1956.
Knapp, FF et al., "Cardiac SPECT with Iodine-123-Labeled Fatty Acids: Evaluation of Myocardial Viability with BMIPP," (1995) J. Nucl. Med. 36(6):1022-10.
Lamki, LM et al., "Radioimaging of Melanoma Using 99m-Tc-labeled Rab Fragment Reactive with a High Molecular Weight Melanoma Antigen," (1990) Canc. Res. (Suppl.) 50:904-908s.
Lear, JL et al., "Improved Tumor Imaging with Radiolabeled Monoclonal Antibodies by Plasma Clearance of Unbound Antibody with Anti-antibody Column," (1991) Radiology 179:509-512.
Marshall et al., "Clearance of circulating radio-antibodies using streptavidin or second antibodies in a xenograft model," (1994) Br. J. Canc. 69:502-507.
Marshall, D. et al., "Galactosylated streptavidin for improved clearance of biotinylated intact and F(ab')2 fragments of an anti-tumour antibody," (1995) Br. J. Canc. 71:18-24.
Meyer, D.L. et al., "Site-Directed Prodrug Activation by Antibody-B-Lactamase Conjugates: Preclinical Investigation of the Efficacy and Toxicity of Doxorubicin Delivered by Antibody Directed Catalysis," (1995) Bioconjugate Chem. 6(4):440-446.
Muzykantov VR et al., "Immunotargeting of antioxidant enzymes to the pulmonary endothelium," (1996) PNAS 93:5213-18, esp 5214, 5217-8.
Norrgren, C. et al., "Evaluation of Extracorporeal Immunoadsorption for Reduction of the Blood Background in Diagnostic and Therapeutic Applications of Radiolabeled Monoclonal Antibodies," (1991) Antibody, Immunoconjugates and Radiopharmaceuticals 4(4):907-914.
Norrgren et al., "A General, Extracorporeal Immunoadsorption Method to Increase the Tumor-to-Normal Tissue Ratio in Radioimmunoimaging and Radioimmunotherapy," (1993) J. Nucl. Med. 34(3):448-454.
Otsuji, E et al., "Decreased renal accumulation of biotinuylated chimeric monoclonal antibody-neocarzionostatin conjugate after administration of avidin," (1997) Chem. Abstracts 126(20): Abstr. 258425, Jp. J. Cancer Res., 1997, 88(2):205-212.
Pispa, J., "Animal Biotinidase," (1965) Annales Medicinae Experimentalis et Biologiae Fenniae 43 (suppl. 5):1-39.
Posner M. et al., "Localization of Cognitive Operations in the Human Brain," (1998) Science 240:1627-31.
Ruth, TJ et al., "Radionuclide Production for the Biosciences," (1989) Nucl. Med. Biol. 16(4):323-336.
Schreiber G.J. et al., "Strategies to Enhance the Localization of Anticancer Immunoconjugates," (1995) Curr. Med. Chemistry 2:616-629.
Sharkey, RM, "Development of a Steptavidin-Anti-Carcinoembryonic Antigen, Antibody, Radiolabeled Biotin Pretargeting Method for Radioimunotherapy of Colorectal Cancer. Studies in a Human Colon Cancer Xenograft Model," (1997) Bioconjugate Chem. 8(4):595-604.
Sinitsyn, VV et al., "Rapid Blood Clearance of Biotinulated IgG after Infusion of Avidin," (1989) J. Nucl. Med. 30(1):66-69.
Spencer, RP et al. eds. (1987) Radionuclides in Therapy (Table of Contents included).
Stolz B. et al., "Regulation of Tumor Celll Growth: Experimental Approaches and Clinical Oncology—Somatostatin Analogues for Somatostatin-Receptor-Mediated Radiotherapy of Cancer," (1996) Digestion 57 (suppl. 1):17-21.
U.S. Appl. No. 10/596,012, filed May 25, 2006, Sandberg et al.
Tutt, A., "Trispecific F(ab)3 derivatives that use cooperative signaling via the TCF/CD3 complex and CD2 to activate and redirect resting cytotoxic cells," (1991) J. Immunol. 147(1):60-69.
Weiden et al. "Pretargeted Radioimmunotherapy (PRIT) for Treatment of non-Hodgekins Lymphoma (NHL): Initial Phase I/II Study Results", (2000) Canc. Biother. Radiopharma. 15(1):15-29.
Wilbur, D.S. et al., "Biotin Reagents for Antibody Pretargeting. Synthesis, Radioiodination, and in Vitro Evaluation of Water Soluble, Biotinidase Resistant Biotin Derivatives," (1997) Bioconjugate Chem. 8:572-584.
Wilbur et al. "Biotin Reagents for Antibody Pretargeting. 4. Selection of Biotin Conjugates for in Vivo Application Based on their Dissociation Rate from Avidin and Streptavidin", (2000) Bioconjugate Chem. 11:569-583.

(56) References Cited

OTHER PUBLICATIONS

Wolf, B. et al., "Biotinidase" (1990) Methods in Enzymology 184:103-111.

Zamora PO et al., "Experimental Radiotherapy of Receptor-Positive Human Prostate Adenocarcinoma with 188Re-RC-160, A Directly-Radiolabeled Somatostatin Analogue," (1999) Int. J. Canc. 65:214-220.

Rosebrough SF, "Plasma Stability and Pharmacokinetics of Radiolabeled Deferoxamine Biotin Derivatives," (1993) J. Pharmacol. Experimental Therapeutics 265(1):408-415.

* cited by examiner

TRIFUNCTIONAL REAGENT FOR CONJUGATION TO A BIOMOLECULE

RELATEDNESS OF THE APPLICATION

This application is a continuation of U.S. application Ser. No. 09/750,280, filed Dec. 29, 2000 now abandoned, which is a continuation of International Application No. PCT/SE1999/01241, filed Jul. 7, 1999, which claims priority to International Application No. PCT/SE1998/001345, filed Jul. 7, 1998. This application is also a continuation-in-part of U.S. application Ser. No. 10/261,040, filed Sep. 30, 2002, now U.S. Pat. No. 7,141,676, which is a continuation in part of U.S. application Ser. No. 09/324,267, filed Jun. 2, 1999 now abandoned, which is a continuation-in-part of U.S. application Ser. No. 08/798,413, filed Feb. 7, 1997 now abandoned, which claims the benefit of U.S. Provisional Application No. 60/011,321, filed Feb. 8, 1996. Each application is incorporated herein by reference in its entirety.

FIELD OF INVENTION

The present invention is directed to a reagent for the conjugation to a biomolecule for the diagnosis and treatment of human and animal conditions or diseases and for the in vitro analysis of affinity labelled biomolecules. More precisely, the present invention is generally directed at a novel chemical reagent which simultaneously conjugate an affinity ligand and an effector agent with a biomolecule to obtain minimal modification of that biomolecule; to a method of diagnosis or treatment of a human or animal condition or disease; and to a kit comprising the reagent according to the present invention. As an example, chemical reagents which contain an affinity ligand (e.g. a biotin moiety), an effector agent (e.g. a radiolabeling moiety), and a biomolecule reactive moiety are coupled together through a trifunctional cross-linking moiety and spaced apart with linker moieties. Using such a reagent, a biomolecule can be biotinylated and radiolabeled via one of two methods, then employed in medical protocols, such as those utilizing extracoporeal immunoabsorptive removal methods to minimize the toxic effects to normal tissue and blood components.

BACKGROUND OF THE INVENTION

Many biomolecules, including proteins and peptides, hold potential as reagents for use in diagnosis and therapy of human conditions and diseases. As most biomolecules do not, by themselves, have properties to make them useful as diagnostic and/or therapeutic reagents, biomolecules of interest are often chemically modified to achieve this. However, one very important criterion must be applied when chemically modifying biomolecules. That criterion is that the modification does not alter the biological property that is important (e.g. cancer cell targeting) in the use of that particular biomolecule. This criterion makes it imperative that site-selective (where possible) and minimal modification of the biomolecule be conducted.

Modification of a targeting biomolecule with an effector agent, such as a radionuclide, can provide valuable new tools for diagnosis and therapy of human and animal diseases or conditions. Coupling of a radionuclide to the biomolecule results in the desired diagnostic effect of providing photons that can be measured or imaged externally to show the localization of the radiolabeled biomolecule, or it may provide the desired therapeutic effect of causing damage to cells or tissues that are targeted by the biomolecule. Biomolecules labeled with photon emitting radionuclides can be used for the diagnosis of a number of human conditions (i.e. extent of myocardial infarcts, presence of cancer, etc.). For example, technetium-99m labeled antibodies can be used to diagnose cancer (Granowska et al. Eur. J. Nucl. Med. 20, 483-489, 1993; Lamki et al. Cancer Res. 50, 904s-908s, 1990; Goldenberg et al. Cancer Res. 50, 909s-921s, 1990); iodine-123 labeled fatty acids can be used to evaluate myocardial perfusion (Corbett J. Nucl. Med. 35, 32s-37s, 1994; Hansen J. Nucl. Med. 35, 38s-42s, 1994; Knapp et al. J. Nucl. Med. 36, 1022-1030, 1995); and fluorine-18 labeled fluorodeoxyglucose can be used to evaluate a variety of functions of the brain (Posner et al., Science 240, 1627-1631, 1988). Biomolecules labeled with particle emissions (e.g. beta, positron, alpha, Auger electrons) can potentially be used for targeted radiotherapy of human disease such as cancer. For example, a large number of monoclonal antibodies (Behr et al. J. Nucl. Med. 38, 858-870, 1997; Divgi et al. J. Nucl. Med. 36, 586-592, 1995; DeNardo et al. Anticancer Res. 17, 1735-1744, 1997) and peptides (Zamora et al. Int. J. Cancer 65, 214-220, 1996; Stolz et al. Digestion 57, 17-21, 1996; Bender et al. Anticancer Res. 17, 1705-1712, 1997) labeled with therapeutic radionuclides such as iodine-131, yttrium-90 and Re-188 are being investigated as new reagents for cancer therapy. Thus, an important modification that can be carried out is to attach a functional moiety to the biomolecule which binds or bonds with a radionuclide. For small (i.e. <2000 Da molecular weight) biomolecules, usually only one radionuclide binding/bonding moiety is site-selectively attached to cause minimal perturbation in its desired biological properties. Larger biomolecules, such as peptides and proteins, may be conjugated with more than one radionuclide binding/bonding moiety before loss of the desired biological properties, but these molecules generally retain more of their desired biological properties when minimal number of conjugations are obtained.

Modification of biomolecules with an "affinity ligand" is also important as it provides a means of coupling two entities together for a variety of in vitro and in vivo applications. By their nature, affinity ligands come in pairs. The preferred affinity ligands used for coupling to the biomolecule must have a high enough binding constant (e.g. $10^6$ $M^{-1}$ or greater) with a second compound to allow the two coupled entities to remain together for a period of time. An example of an affinity ligand pair is a monoclonal antibody and its hapten. The affinity ligand pairs of biotin/avidin and biotin/streptavidin are often used with biomolecules. The very strong interaction (i.e. $K=10^{13}$-$10^{15}$ $M^{-1}$) of biotin with the proteins avidin and streptavidin (Green, Methods Enzymol. 184, 51-67, 1990; Green, Adv. Prot. Chem. 29, 85-133, 1975) provides a foundation for their use in a large number of applications, both for in vitro and in vivo uses. While the proteins avidin and streptavidin are sometimes conjugated with biomolecules, conjugation of biotin introduces less perturbation of the biomolecule, and more than one biotin molecule can be conjugated with minimal affect on the biomolecule. Therefore, the preferred affinity label is biotin or a derivative thereof, and the examples herein are reflective of this preference. As with the radionuclide binding/bonding moiety, it is important to minimize the number of affinity ligands (e.g. biotin conjugates) attached to a biomolecule to retain the desired biological properties.

Modification of the biomolecule by attachment (conjugation) of another molecule to a particular reactive functional group (e.g. amine, sulfhydryl, aldehyde, ketone) precludes attachment of a second molecule to that group. Thus, if attachment of more than one type of molecule to a biomolecule is desired (to impart two functions), the attachment must be made at a second site using currently available reagents. Since in some applications, it is desirable to have both an affinity ligand and an effector agent (e.g. a moiety that binds/bonds with a radionuclide), site-selective conjugation is precluded. Further, modification of biomolecules that are not made in a site-selective manner (e.g. reaction with surface amine groups in proteins) are limited due to the fact that two different sites are modified. Additionally, modification of larger biomolecules (e.g. proteins) in two subsequent steps can result in a heterogeneous population of modified biomolecules in which molecules that contain the second conjugated species may have less of the desired biological properties (i.e. tumor targeting) than those that do not contain the second conjugate. This can result in a subgroup of biomolecules containing both conjugated species that do not have the properties desired. To circumvent these problems, the affinity ligand (e.g. biotin moiety) and an effector agent (e.g. radionuclide binding/bonding moiety with or without the radionuclide) can be coupled together through trifunctional crosslinking reagent to form a new type of reagent. With the use of this new class of reagents, an equal number of affinity ligands and radionuclide binding/bonding moieties will be conjugated to the biomolecule. With a combined affinity ligand and radiolabeling compound, site specific addition of both reagents can be made, and minimization of the number of conjugates to the biomolecule can be attained. Linking an affinity ligand such as biotin to a fluorescent moiety which is further attached to an oligosaccharide is described in Varki et al., WO 94/28008. The issue of attaching an affinity ligand to cytotoxic agent or an agent which can convert a prodrug to an active drug, and where either of these are further attached to a targeting molecule, is addressed in Nilsson et al., U.S. patent application Ser. No. 08/090 047. However, none of these publications neither alone or in combination describe or indicate the present innovation. The issue of combining an affinity reagent and effector agent on one molecule to achieve minimal modification of biomolecules is not unique to biotin (as the affinity ligand) or radionuclide binding/bonding moieties (the effector agent), and is not limited to only one affinity ligand and one effector ligand per molecule. Combinations of more than one affinity ligand and/or more than one affinity ligand per molecule may be advantageous for certain applications.

The radiolabeled and affinity ligand conjugated biomolecule products obtained from this invention are useful in many in vitro and in vivo applications. A preferred application, where the biomolecule is a tumor binding monoclonal antibody, toxin conjugate, or enzyme conjugate, the affinity ligand is biotin or a derivative thereof, and the radionuclide is a diagnostic or therapeutic radionuclide used in a patient cancer treatment protocol, is to use a biotin binding (e.g. avidin coated) column for extracorporeal immunoabsorptive removal of a radiolabeled antibody conjugate from a patient's blood. Extracorporeal removal of the radiolabeled antibody, toxin conjugate, or enzyme conjugate limits the toxic effects of the radioactivity, toxin, or enzyme to specifically targeted tissues, minimizing the exposure time and interaction with non-target tissues. Importantly, to be effective, medical agents (e.g. biomolecules) must exert their pharmacological action on a particular target tissue or group of target cells. Targeting of such agents is most often carried out by systemic administration (i.e. intravenous injection) which means that they will be transported through the blood and lymph system to most parts of the body. This transportation, or circulation, of the medical agent throughout the body can result in undesirable toxic side effects in tissues or organs other than those where the effect of the agents is beneficial to the patient.

Specific tissue or organ localization of a medical agent is a very important factor in its effective application. Lack of specific tissue localization is of particular importance in the treatment with medical agents where the desired effect is to kill certain types of cells such as in the treatment of cancer. In order to increase the specificity and thereby make the cancer therapy more effective, tumor marker specific targeting agents such as cancer cell binding monoclonal antibodies have been used as carriers for various cell toxic agents (immunoconjugates) such as, but not limited to, radionuclides, cytotoxins, and enzymes used in prodrug protocols (Meyer et al., Bioconjugate Chem. 6, 440-446, 1995; Houba et al., Bioconjugate Chem. 7, 606-611, 1996; Blakey et al., Cancer Res. 56, 3287-3292, 1996). Although, monoclonal antibodies are selectively bound with tumor cells over non-tumor cells, an initial high concentration of the toxic immunoconjugate is required to optimize binding of a particular agent with tumors in a patient. While required for optimal therapy of the cancer, the high concentration of cytotoxic material in blood and non-target tissues causes undesirable side-effects on sensitive and vital tissues like the bone marrow. Various methods have been proposed to rapidly clear these agents from blood circulation after that the tumor has received a maximum dose of the immunoconjugate. Some blood clearance methods involve the enhancement of the bodies own clearing mechanism through the formation of various types of immune complexes. Similarly, blood clearance can be obtained by using molecules that bind with the immunoconjugate, such as monoclonal antibodies (Klibanov et al., J. Nucl. Med. 29, 1951-1956, 1988; Marshall et al., Br. J. Cancer 69, 502-507, 1994; Sharkey et al. Bioconjugate Chem. 8, 595-604, 1997), (strept)avidin (Sinitsyn et al., J. Nucl. Med. 30, 66-69, 1989; Marshall et al., Br. J. Cancer 71, 18-24, 1995), or biotin containing compounds which also contain sugar moieties recognized by the asialoglycoprotein receptor on liver cells (Ashwell and Morell, Adv. Enzymol. 41, 99-128, 1974). Other methods involve means of removing the circulating immunoconjugates through extracorporeal methods (see review article by Schriber G. J. & Kerr D E, Current Medicinal Chemistry, 1995, Vol. 2, pp 616-629).

The extracorporeal techniques used to clear a medical agent from blood circulation is particularly attractive. Extracorporeal devices for this application have been described (Henry C A, 1991, Vol. 18, pp. 565; Hofheinz D et al, Proc. Am. Assoc. Cancer Res. 1987 Vol. 28, pp. 391; Lear J L, et al. Radiology 1991, Vol. 179, pp. 509-512; Johnson T K, et al. Antibody Immunoconj. Radiopharm. 1991, Vol. 4, pp. 509; Dienhart D G, et al. Antibody Immunoconj. Radiopharm. 1991, Vol. 7, pp. 225; DeNardo G L, et al. J. Nucl. Med. 1993, Vol. 34, pp. 1020-1027; DeNardo G L, et al. J. Nucl. Med. 1992b, Vol. 33, pp. 863-864; DeNardo S. J., et. al. J. Nucl. Med. 1992a, Vol. 33, pp. 862-863. U.S. Pat. No. 5,474,772; Australian patent 638061, EPO 90 914303.4 of Maddock, describe these methods.

To make the blood clearance more efficient and to enable processing of whole blood, rather than blood plasma, the medical agent (e.g. tumor specific monoclonal antibody carrying cell killing agents or radionuclides for tumor localization) have been biotinylated and cleared with the use of an affinity (e.g. biotin-binding) column. A number of publications provide data which show that this technique is both efficient and practical for the clearance of biotinylated and radionuclide labeled tumor specific antibodies (Norrgren K, et al. Antibody Immunoconj Radiopharm 1991, Vol. 4, pp. 54; Norrgren K, et. al. J. Nucl. Med. 1993, Vol. 34, pp. 448-454

Garkavij M, et. al. Acta Oncologica 1996, Vol. 53, pp. 309-312; Garkavij M, et. al. J. Nucl. Med. 1997, Vol. 38, pp. 895-901). U.S. patent application Ser. No. 08/090,047, EPO 92 903 020.3 of Nilsson and Ser. No. 08/434,889 of Maddock describe these applications.

SUMMARY OF THE INVENTION

The object of the present invention is to eliminate the above mentioned problems in the art. This object is achieved with a reagent as described by way of introduction and having the features defined by the characterising part of claim 1. Preferred embodiments are presented in the subclaims.

In general, the invention discloses a new type of compound which combines an affinity ligand and an effector agent in a single molecule that can be used to modify biomolecules. The modified biomolecules are themselves new entities in that fewer sites on them are modified than obtainable with previous reagents. More specifically, the invention describes the chemical components and examples of a new type of molecule (shown in schematic structure (I)) that can be used to conjugate an affinity ligand, such as biotin, and concurrently conjugate an effector ligand, such as a radionuclide binding/bonding moiety with/without a radiolabel, to a biomolecule of interest for a variety of diagnostic and therapeutic applications. This invention also discloses two approaches to the attaching both affinity ligands and radionuclides to a biomolecule (i.e. preformed and postformed labeling approaches) in accordance to the routes shown in Scheme II. For therapeutic applications, a preferred method of blood clearance of the new medical agent (conjugated biomolecule), using extracoporeal immunoabsorptive columns is disclosed.

Further, the new reagent according to the present invention can also be used for in vitro analysis of affinity labelled biomolecules, e.g. monoclonal antibodies or derivatives thereof, labelled with e.g. biotin or derivatives thereof. Thus, due to the presence of a photoactive agent, e.g. a chromophore or a fluorophore, as effector agent in the reagent molecule, it is possible to determine the amount of affinity label bound to the biomolecule as this amount is proportioned to the amount of photoactive agent.

DETAILED DESCRIPTION

General structure of compounds disclosed. The chemical nature of a compound for concurrent conjugations of an affinity ligand and an effector agent is shown graphically in the schematic structure (I). A brief description of the various parts of the generalized formulation is provided in the text following the schematic structure (I):

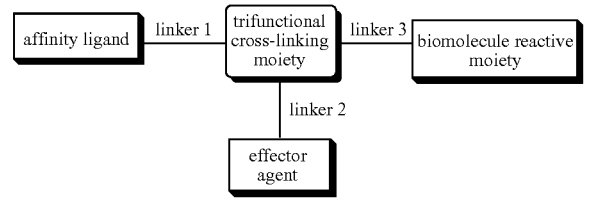

The term "affinity ligand" used throughout the description and the claims means any moiety that binds with another molecule with an affinity constant of $10^6$ $M^{-1}$ or higher. A preferred affinity ligand is a biotin moiety which can be biotin, or any derivative or conjugate of biotin that binds with avidin, streptavidin, or any other biotin binding species.

The term "effector agent" used throughout the description and the claims means a radionuclide binding moiety with or without the radionuclide, a synthetic or naturally occurring toxin, an enzyme capable of converting pro-drugs to active drugs, immunosuppressive or immunostimulating agents, or any other molecule known or found to have a desired effect, directly or indirectly, on cells or tissues.

The term "biomolecule reactive moiety" used throughout the description and the claims means any moiety that will react with a functional group naturally occurring or synthetically introduced on a biomolecule.

The term "trifunctional cross-linking moiety" used throughout the description and the claims means any chemical moiety that can combine the affinity ligand (e.g. biotin moiety), effector agent (e.g. radionuclide binding/bonding moiety) and a biomolecule reactive moiety.

The term "linker 1" used throughout the description and the claims means a chemical moiety that is an attaching moiety and spacer between the trifunctional cross-linking moiety and the biotin moiety such that binding with avidin or streptavidin, or any other biotin binding species, is not diminished by steric hindrance. Linker 1 may also impart increased water solubility and biotinidase stabilization.

The term "linker 2" used throughout the description and the claims means a chemical moiety that is used to attach the radionuclide binding moiety to the trifunctional cross-linking moiety. Linker 2 may also impart increased water solubility.

The term "linker 3" used throughout the description and the claims means a chemical moiety used to attach the biomolecule reactive moiety to the trifunctional cross-linking moiety. Linker 3 may not be required, but may be advantageous in some cases. Linker 3 may be used as a spacer and/or it may be used to increase the water solubility of the compound.

Affinity Ligand.

The preferred affinity ligand is biotin or a derivative thereof. In most examples the biotin moiety will be natural biotin 1, which is coupled to linker 1 through an amide bond. In some examples it may be advantageous to have a biotin derivative that does not bind as tightly as natural biotin, or a biotin derivative that binds to chemically modified, or genetically mutated, avidin or streptavidin in preference to natural biotin. Examples of such biotins are norbiotin 2, homobiotin 3, oxybiotin 4, iminobiotin 5, desthiobiotin 6, diaminobiotin 7, biotin sulfoxide 8, and biotin sulfone 9. Other modifications of biotin, including further modification of 2-9, are also included.

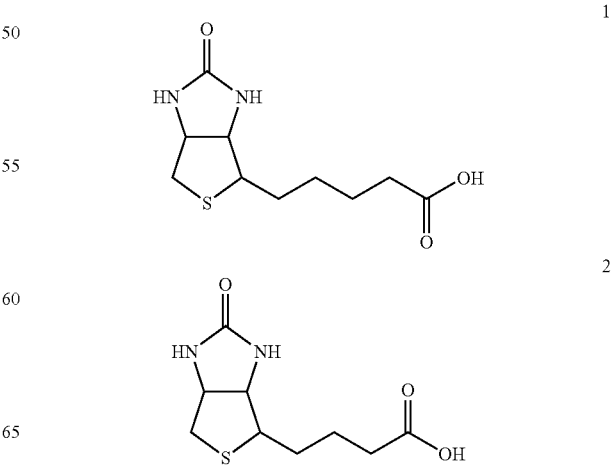

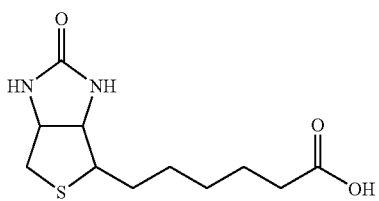

3

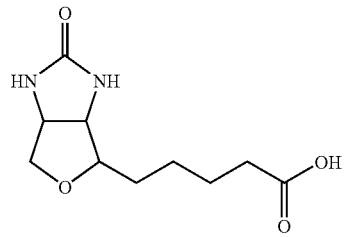

4

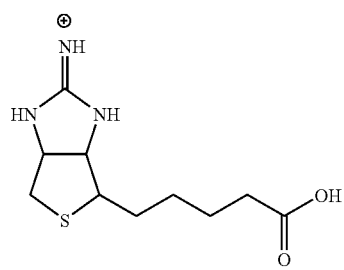

5

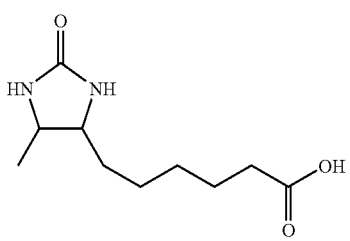

6

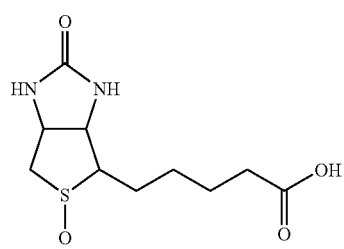

7

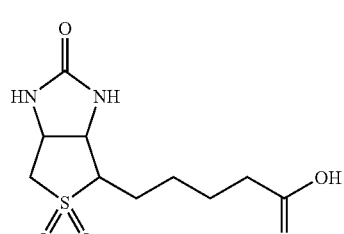

8

Effector Agent.

The preferred effector agent is a radionuclide binding/bonding moiety, with or without the radionuclide being present. There are a large number of radionuclides that are potentially useful for diagnostic and therapeutic purposes (see articles in Spencer et al. eds., Radionuclides in Therapy, CRC Press, 1987; Ruth et al., Nucl. Med. Biol. 16, 323-336, 1989), and thus moieties which bind or bond with them may be incorporated as the radionuclide binding/bonding moiety. Examples of gamma imaging radionuclides include, Tc-99m, In-111, and I-123. Examples of positron imaging radionuclides include Ga-68, F-18, Br-75, Br-76, and I-124. Examples of therapeutic radionuclides include Y-90, I-131, Re-186, Re-188, Cu-67, Sm-153, Lu-177, Bi-212, Bi-213 and At-211. It is a requirement that the radionuclides be bound by chelation (for metals) or covalent bonds in such a manner that they do not become separated from the biotinylation/-radiolabeling compound under the conditions that the biomolecule conjugates are used (e.g. in patients). Thus, the most stable chelates or covalent bonding arrangements are preferred. Examples of such binding/bonding moieties are: aryl halides and vinyl halides for radionuclides of halogens; $N_2S_2$ 9 and $N_3S$ 10 chelates for Tc and Re radionuclides; amino-carboxy derivatives such as EDTA 11, DTPA 12, derivatives Me-DTPA 13 and cyclohexyl-DTPA 14, and cyclic amines such as NOTA 15, DOTA 16, TETA 17, CITC-DTPA (not shown, U.S. Pat. No. 4,622,420), and triethylene-tetraaminehexaacetic acid derivatives (not shown, see Yuang-fang and Chuanchu, Pure & Appl. Chem. 63, 427-463, 1991) for In, Y, Pb, Bi, Cu, Sm, Lu radionuclides. Attachment of the radionuclide binding/bonding moiety to linker 2 can be achieved at a number of locations in the moieties.

The effector agent can also be a photoactive compound or a compound which can be converted to a photoactive compound, such as a chromophore, fluorophore or any other conventionally used photoactive compound.

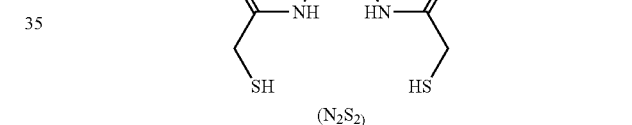

9

(N₂S₂)

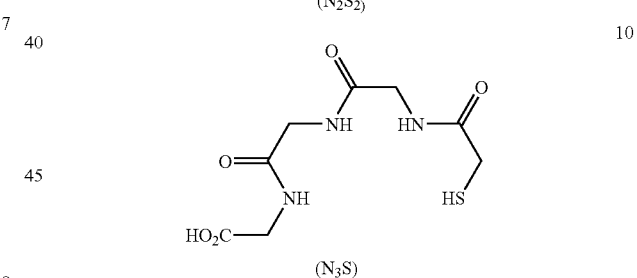

10

(N₃S)

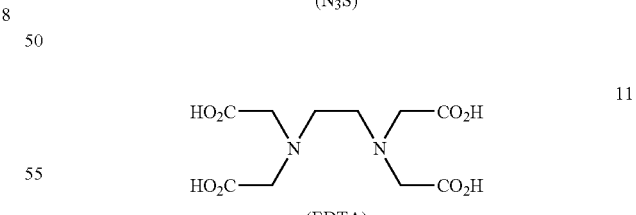

11

(EDTA)

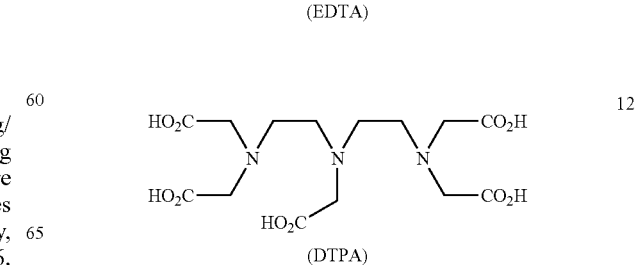

12

(DTPA)

-continued

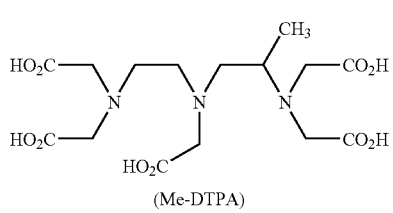

(Me-DTPA)

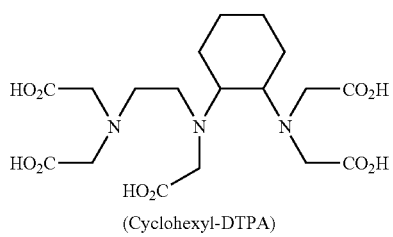

(Cyclohexyl-DTPA)

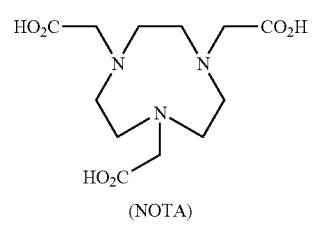

(NOTA)

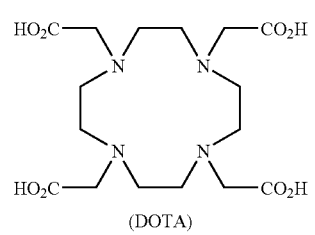

(DOTA)

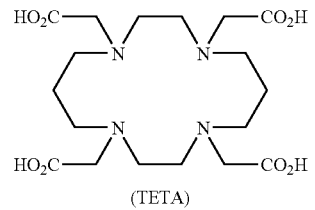

(TETA)

Biomolecule Reactive Moiety.

There are a number of moieties that are reactive with functional groups that may be present on a biomolecule, e.g. a protein. For example, aryl or alkyl activated carboxylic acids can be reacted with nucleophilic groups such as primary or secondary amines. Such activated esters include: N-hydroxysuccinimide esters 18, sulfo-N-hydroxysuccinimide esters 19, phenolic esters (e.g. phenol 20, p-nitrophenol 21, tetrafluorophenol 22). Other amine reactive groups include aryl and alkyl imidates 23 and alkyl or aryl isocyanates or isothiocyanates, 24. Sulfhydryl groups on the biomolecule can be reacted with maleimides 25 or alpha-haloamide 26 functional groups. Biomolecules containing naturally occurring or synthetically produced (e.g. by conjugation or from oxidized sugar moieties) aldehydes and ketones can be reacted with aryl or alkyl hydrazines 27, aryl or alkyl acylhydrazines 28, alkyl or aryl hydroxylamines 29.

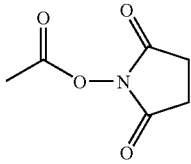

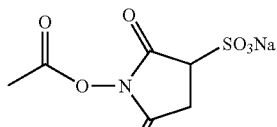

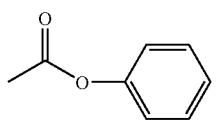

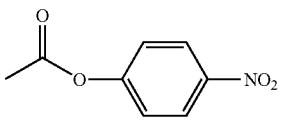

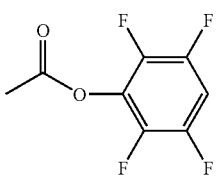

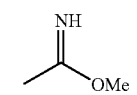

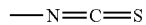

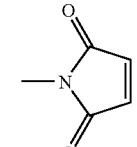

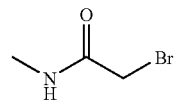

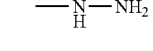

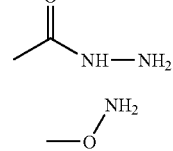

Trifunctional Cross-Linking Moiety.

The trifunctional cross-linking moiety has two functional groups that can be used to couple with linker 1 and linker 2. It has another functional group that can be either converted directly into the biomolecule reactive moiety or coupled with linker 3. Examples of preferred trifunctional cross-linking moieties are triaminobenzene 30, tricarboxybenzene 31, dicarboxyaniline 32, and diaminobenzoic acid 33. If the functional groups present on the cross-linking

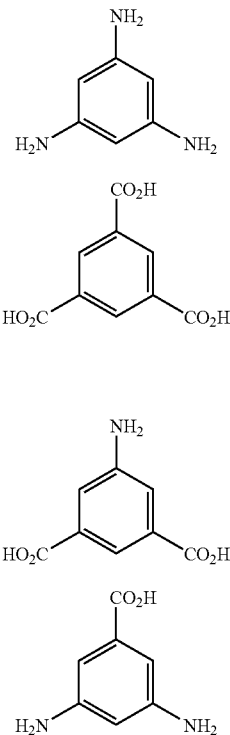

moiety are not by themselves reactive with a functional group on the biomolecule, then they are converted into more reactive moieties, such as activated esters (for carboxylic acids), imidates (cyano functional groups), maleimides (amino), isocyanates, isothiocyanates, etc. The functional groups present on the cross-linking moiety may vary, and protection/deprotection/activation steps may be required to synthesize the desired compound. A trifunctional cross-linking moiety is preferred, but in those examples where more than one effector agent, affinity ligand, or protein reactive moiety is advantageous, tetrafunctional, or higher, cross-linking moieties may be applied.

Linker Moieties.

The linker moieties function as spacers and also may aid in water solubilization for compounds that do not contain ionized or ionizable functionalities. Linker 1 must provide ample space between the biotin moiety and the trifunctional cross-linking moiety such that there is a minimum of 9 Å for biotin binding with avidin or streptavidin. Extended linkers (e.g. 6-20 atoms in length) are preferred to assure that there is no steric hindrance to binding avidin or streptavidin from the biomolecule that the conjugate is attached to. The extended linkers may contain hydrogen bonding atoms such as ethers or thioethers, or ionizable groups such as carboxylates, sulfonates, or ammonium groups, to aid in water solubilization of the biotin moiety. Many of the biotin moieties are highly insoluble in water. When the compounds of this invention are used in serum or in animals or people, there is an additional requirement for a linker attached to biotin that is not required for linkers attached to other moieties. This requirement is to provide a means of blocking the enzyme biotinidase (Wolf et al., Methods Enzymol. 184, 103-111, 1990; Pipsa, Ann. Med. Exp. Biol. Fenn 43, Suppl. 5, 4-39, 1965) from cleaving the amide bond (biotinamide) to release biotin. This requirement is met by altering the distance between the bicyclic rings of the biotin moiety (as in norbiotin or homobiotin) or using a biotin derivative that has a dramatically decreasing binding with avidin or streptavidin (e.g. desthiobiotin). If natural biotin is used, blockade of biotinidase activity is provided by introducing an alpha carboxylate (Rosebrough, J. Pharmacol. Exp. Ther. 265, 408-415, 1993) or an N-methyl group (Wilbur et al., Bioconjugate Chem. 8, 572-584, 1997) in Linker 1.

Linker 2 must provide a means of coupling an effector agent, such as a radionuclide binding/bonding moiety, with the trifunctional cross-linking moiety. The nature of linker 2 can be highly dependent on the chemistry associated with effector agent employed, particularly in the case where the effector agent is a radionuclide binding/bonding moiety. Although linker 2 may be as short as 1 atom, it is preferred to have more space than 1 atom provided to decrease the steric environment around the affinity ligand (e.g. biotin moiety). Linker 2 can also have the water solubilizing atoms or groups of atoms to increase water solubility. Linker 3, if required, provides additional space between the biomolecule and the biotin moiety, and can be used to provide additional water solubilization where required. Examples of preferred non-ionized linkers include the trioxadiamine 34 and dioxadiamine 35. Examples of preferred ionized linkers include aryl diaminosulfonate 36 and aryl diaminotrimethylammonium 37. Examples of linkers that also contain a biotinidase blocking moiety are made by combining one of the linkers 34-37 with another molecule, for example combining linker 34 with N-methylglycine to yield linker 38, where the N-methyl end must be attached to the biotin moiety to impart stability towards biotinidase cleavage.

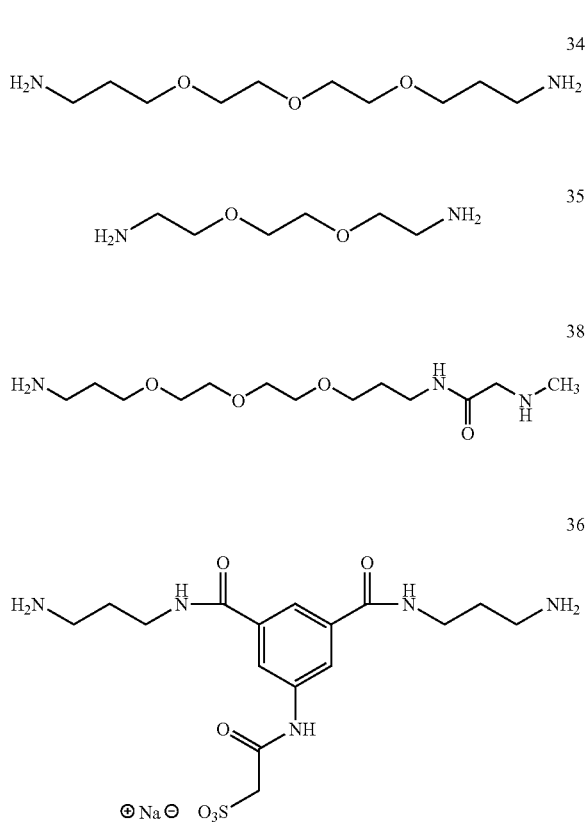

37

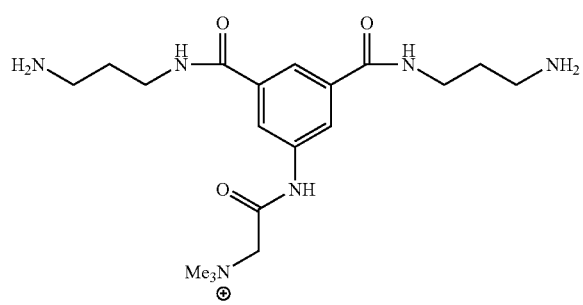

This invention discloses new chemical species that are composed of any combination of affinity ligands (e.g. biotin moieties), effector agents (e.g. radionuclide binding moieties), protein reactive moieties, trifunctional cross-linking moiety, and linking moieties. In specific examples, the reagents of this invention (generically shown in schematic structure (I)) provide a means of biotinylation and radiolabeling of biomolecules. This results in a minimally modified biomolecule (MMB). Irrespective of the individual components of the new chemical species, the process of conjugation and radiolabeling can occur by two distinctly different methods to give the same final product (the MMB), as depicted in Scheme (II) below. Path A is termed postformed conjugate (radio)labeling and Path B is termed preformed conjugate (radio)labeling. Path A, where a compound of this invention is conjugated with the biomolecule first, and subsequently radiolabeled with the radionuclide chosen, is the preferred method of conjugation and radiolabeling. However, some radionuclide binding/bonding conditions are not compatible with certain biomolecules, therefore, Path B may be used as an alternative approach.

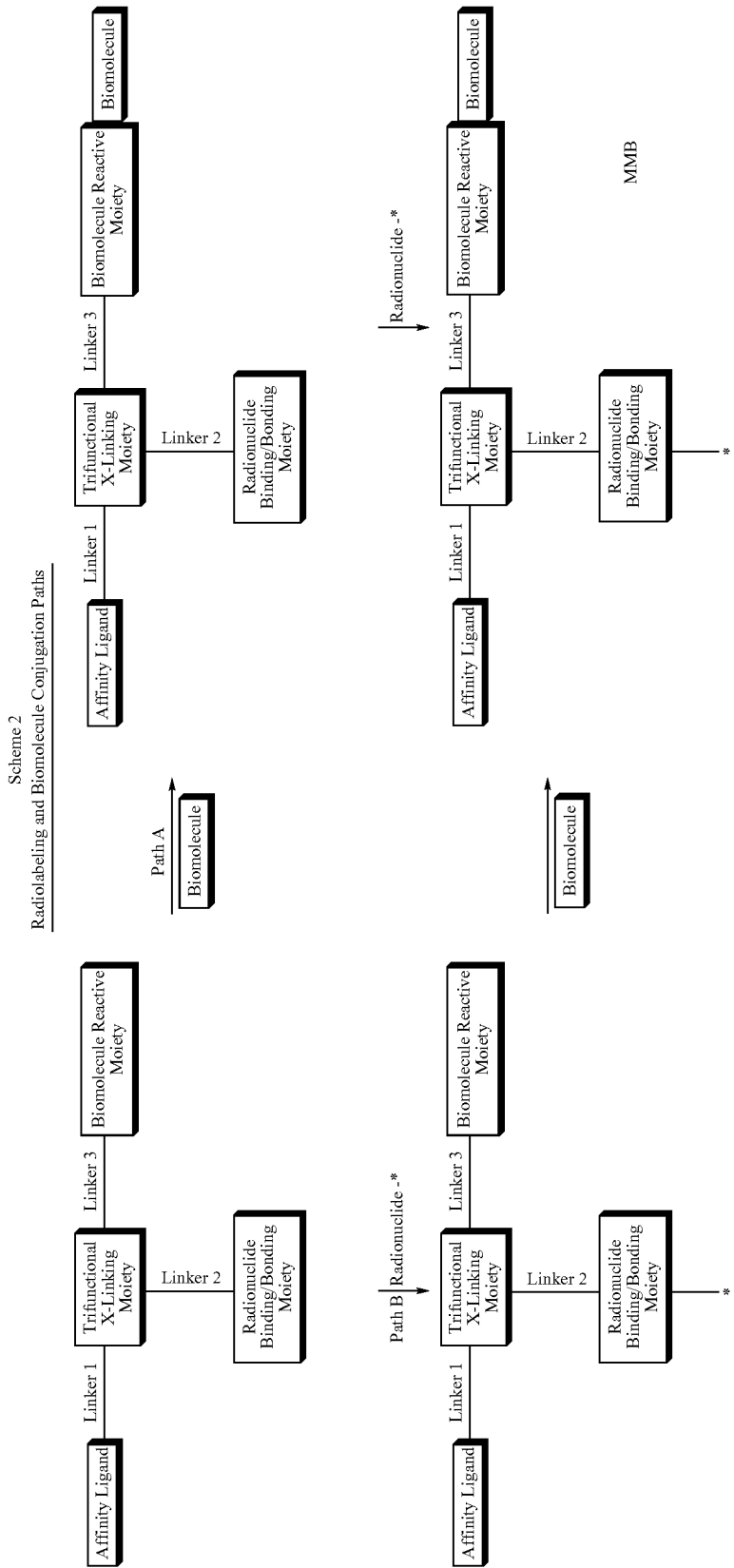

EXAMPLES

The following examples 1-7 are provided to show some of the different combinations of reagents that are disclosed herein, and to show methods for preparing them. The examples are provided by way of illustration, not by way of limitation. Many further examples can be made by differing combinations of chemical moieties as depicted in the general formulation. The examples 1-6 are followed by reaction schemes relating to each example for the production of the reagents 39-44 according to the present invention.

Example 1

Compound 39 is a reagent according to the present invention and contains biotin as the biotin moiety; a biotinidase stabilized linker as linker 1; aminoisophthalic acid as the trifunctional cross-linking moiety; a CHX-DTPA group as a chelator for In-111 and Y-90; an aminobenzyl group for linker 2; no linker 3; and an isothiocyanate biomolecule reactive moiety. A method for synthesizing 39 from previously known reagents is provided.

Example 2

Compound 40 is a reagent according to the present invention and contains biotin as the biotin moiety; a biotinidase stabilized (N-methyl) linker as linker 1; aminoisophthalic acid as the trifunctional cross-linking moiety; a tri-n-butylstannylbenzoate group as a moiety that is rapidly reacted to bond with the radiohalogens Br-75/76/77, I-123/124/125/131, or At-211; a trioxadiamine for linker 2; no linker 3; and a tetrafluorophenyl ester biomolecule reactive moiety. A method for synthesizing 40 from previously known reagents is provided.

Example 3

Compound 41 is a reagent according to the present invention and contains homobiotin as the biotin moiety; a trioxadiamine linker as linker 1; aminoisophthalic acid as the trifunctional cross-linking moiety; an acid labile protected $N_2S_2$ group as a chelator for Tc-99m or Re186/188; an propionate moiety for linker 2; no linker 3 and a tetrafluorophenyl ester biomolecule reactive moiety. A method for synthesizing 41 from previously known reagents is provided.

Example 4

Compound 42 is a reagent according to the present invention and contains homobiotin as the biotin moiety; a trioxadiamine linker as linker 1; aminoisophthalic acid as the trifunctional cross-linking moiety; a BAT group as a chelator for Tc-99m or Re-186/188; a pentyloxybenzoate group for linker 2; no linker 3 and a tetrafluorophenyl ester biomolecule reactive moiety. This example is shown in that the BAT chelate allows the reagent to be coupled with a biomolecule (e.g. protein) prior to attaching the radionuclide. Modification Path A. A method for synthesizing 42 from previously known reagents is provided.

Example 5

Compound 43 is a reagent according to the present invention and contains biotin as the biotin moiety; a biotinidase stabilized linker as linker 1; aminoisophthalic acid as the trifunctional cross-linking moiety; a TETA group as a chelator for Cu-67; an amibenzyl group for linker 2; no linker 3; and an isothiocyanate biomolecule reactive moiety. A method for synthesizing 43 from previously known reagents is provided.

Example 6

Compound 44 is a reagent according to the present invention and contains biotin as the biotin moiety; a biotinidase stabilized linker as linker 1; tricarboxybenzene as the trifunctional cross-linking moiety; a tri-n-butylstannylbenzoate moiety for reaction with radiohalogens; a trioxadiamine moiety for linker 2; a trioxadiamine moiety for linker 3; and a maleimide group as the biomolecule reactive moiety. A method for synthesizing 44 from previously known reagents is provided.

Example 7

Compound 45 is a reagent according to the present invention and contains biotin as the biotin moiety; a biotinidase stabilized linker (the glycyl moiety is replaced by an aspartyl moiety as linker 1; aminoisophthalic acid as the trifunctional cross-linking moiety; a CHX-A"-DTPA group as a chelator for In-111, Y-90 and Bi-213; an aminobenzyl group for linker 2; no linker 3; and an isothiocyanate biomolecule reactive moiety. The synthesis sequence of reactions to prepare this compound are shown in scheme 7.

Example 1

Reagent with Biotin, Biotinidase Stabilizing Linker, CHX-DTPA Chelate, and Isothiocyanate

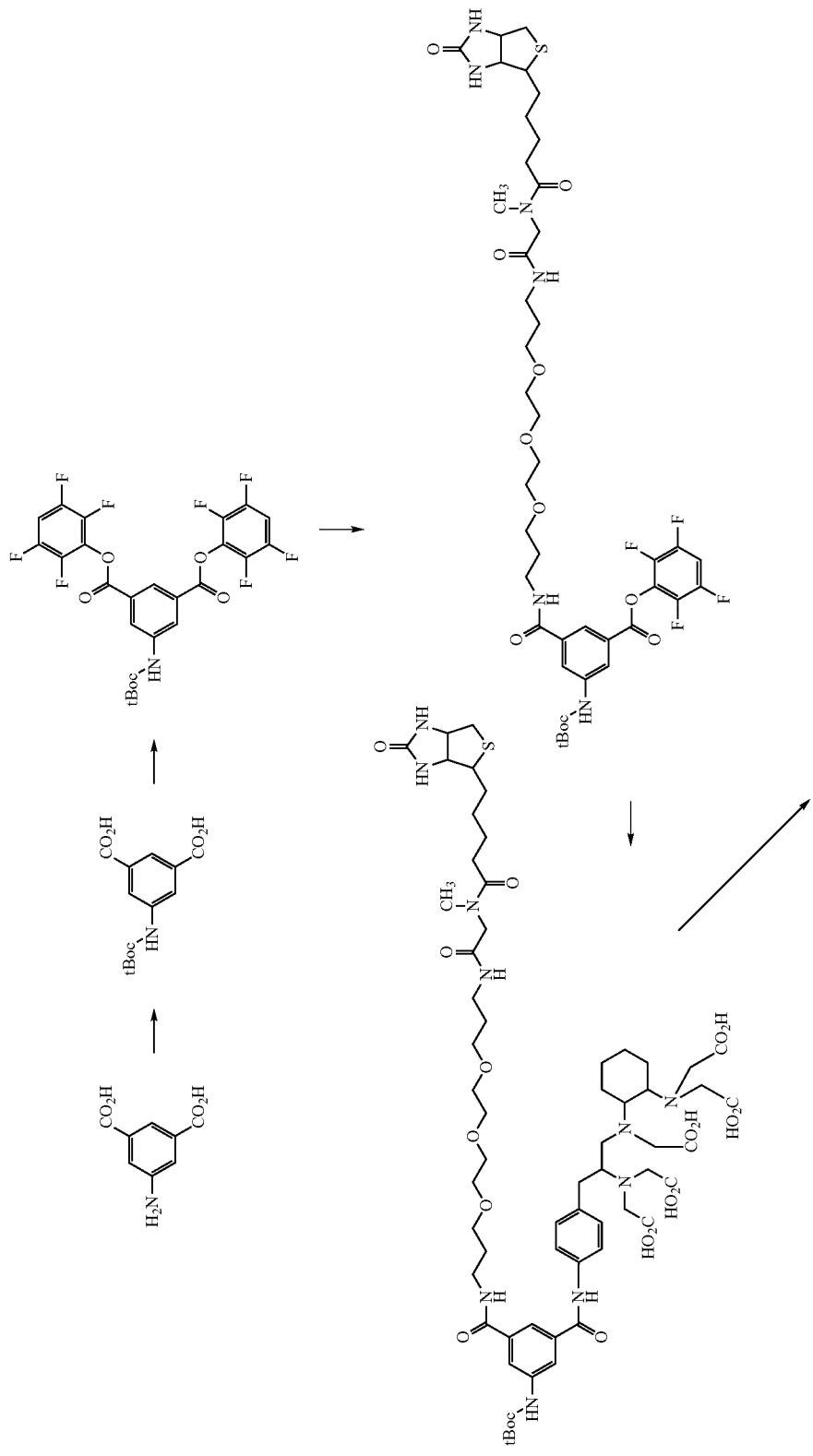

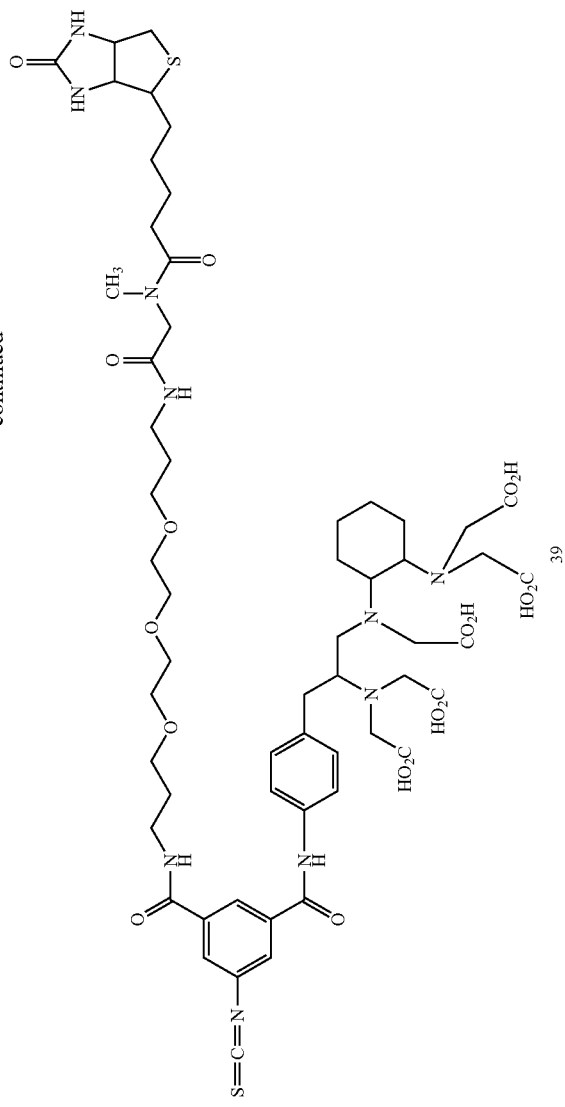

Example 2

Reagent with Biotin, Biotinidase Stabilized Linker, Arylstannane Radiohalogenation Moiety, and Tetrafluorophenyl Ester

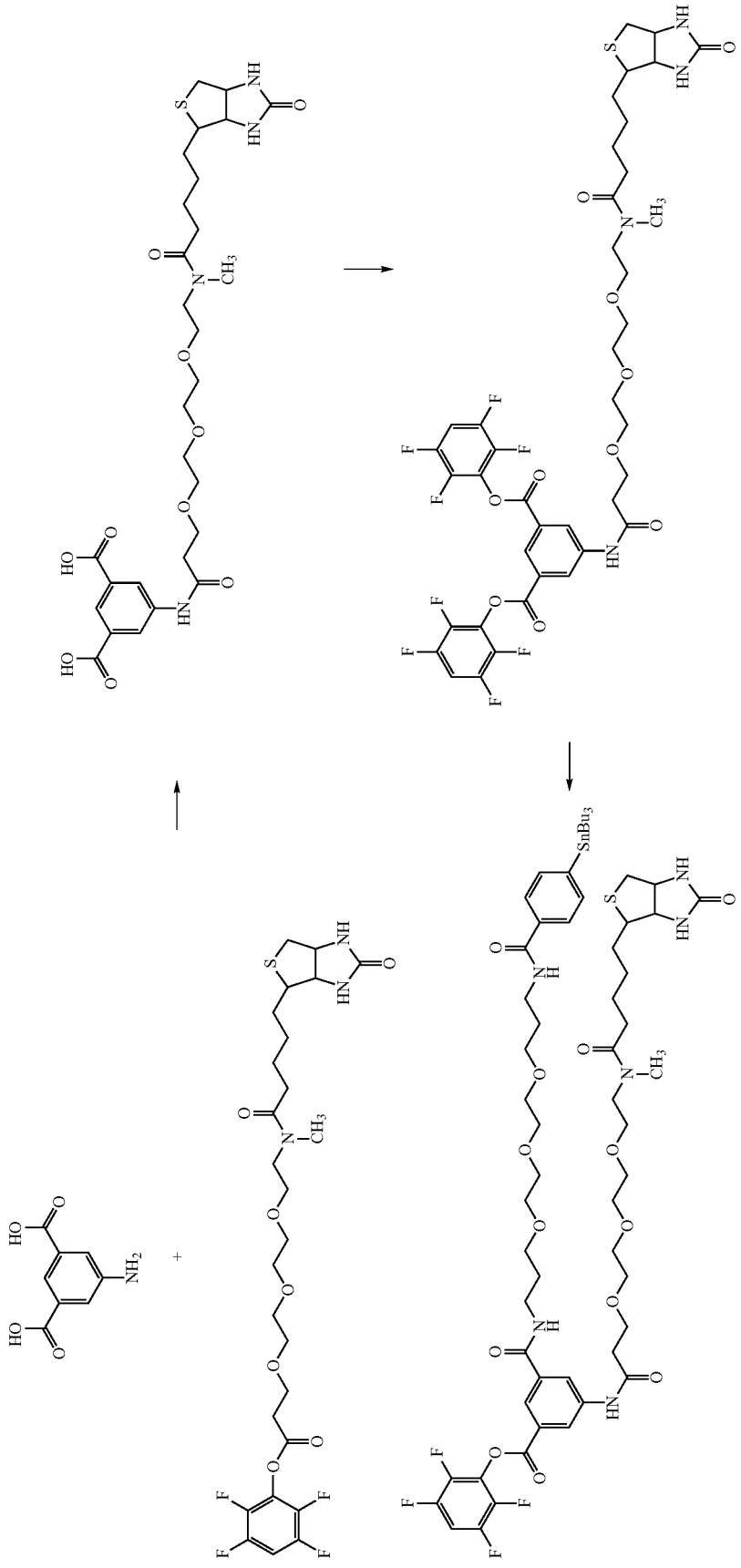

Example 3
Reagent with Homobiotin, DiamidoDithio ($N_2S_2$) Chelate, and Tetrafluorophenyl Ester
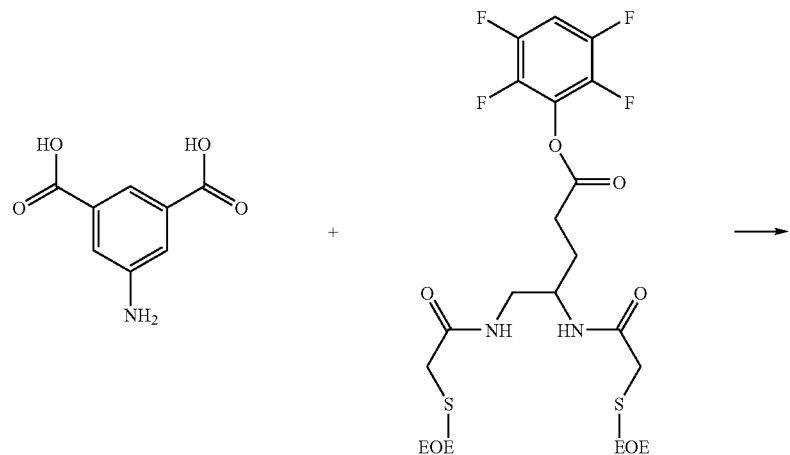
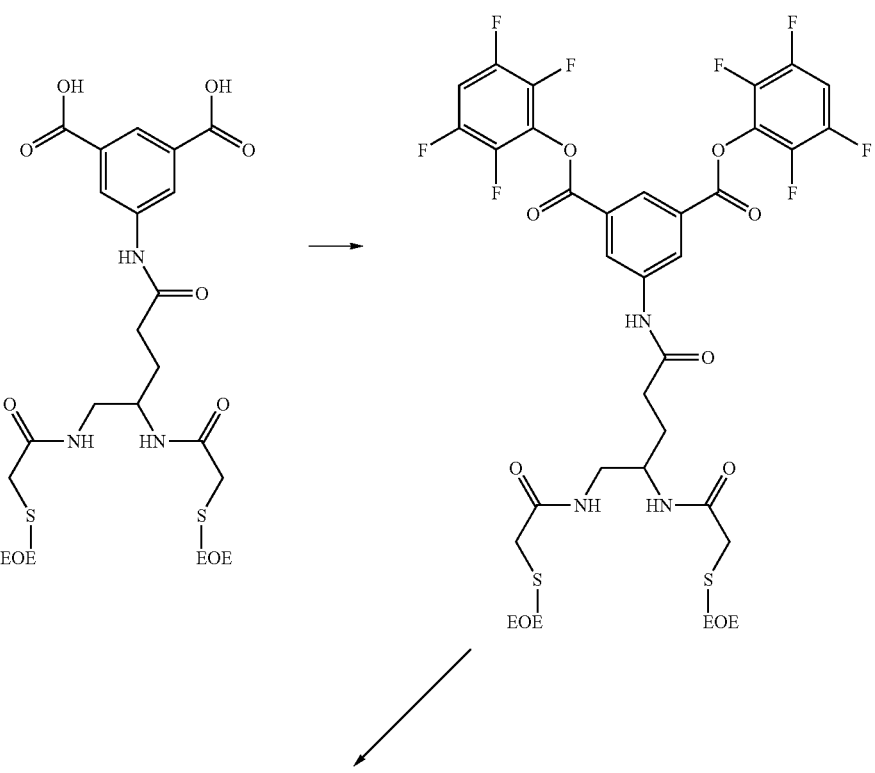

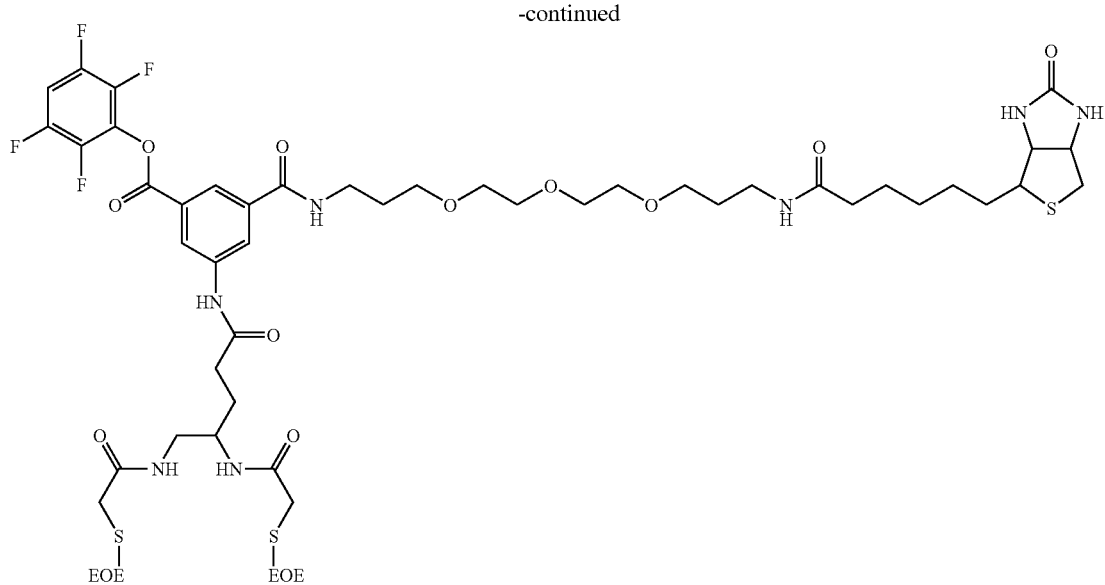
41
Example 4
Reagent with Homobiotin, DiaminoDithio ($N_2S_2$) Chelate, and Tetrafluorophenyl Ester
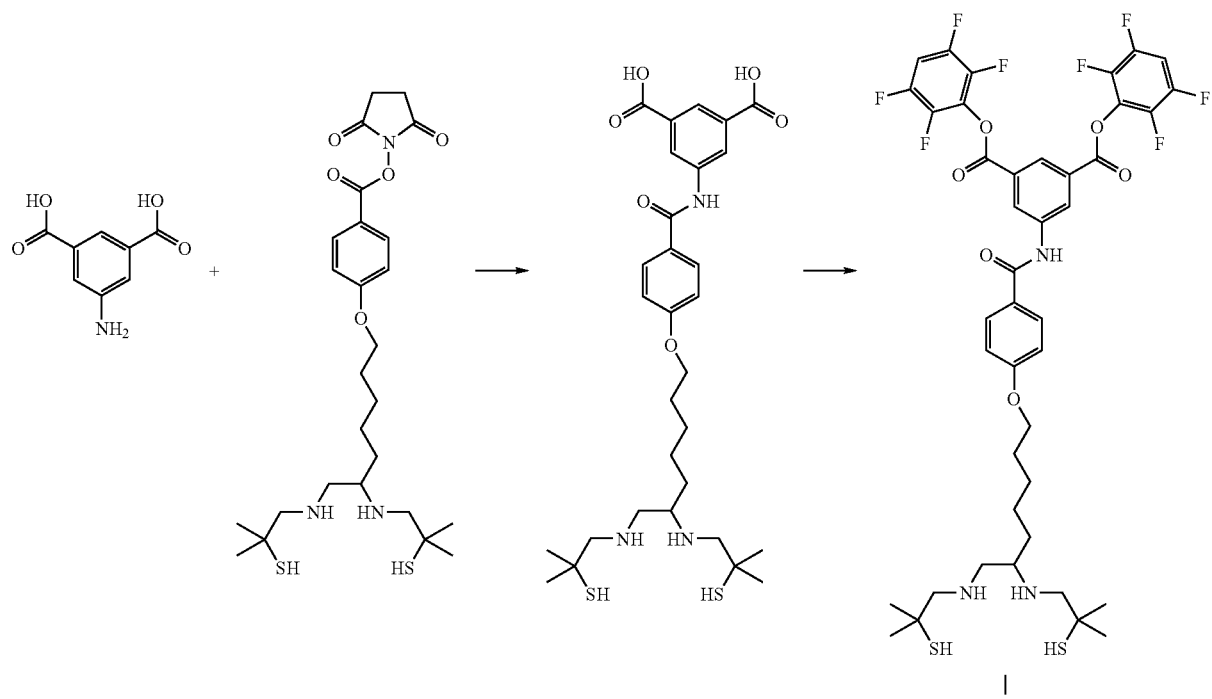

-continued
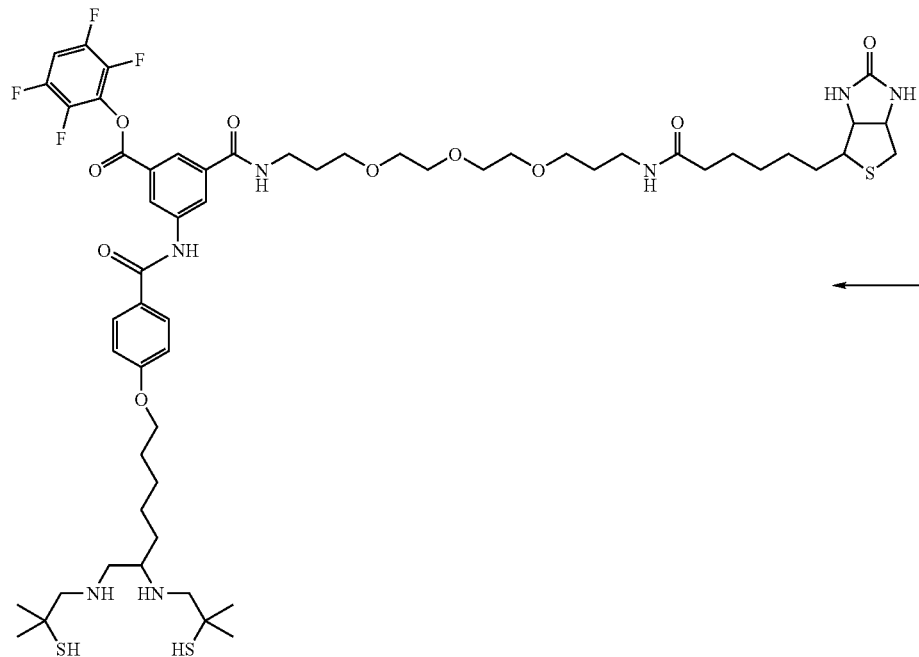
42
Example 5
35
Reagent with Biotin, Biotinidase Stabilizing Linker, TETA Chelate, and Isothiocyanate

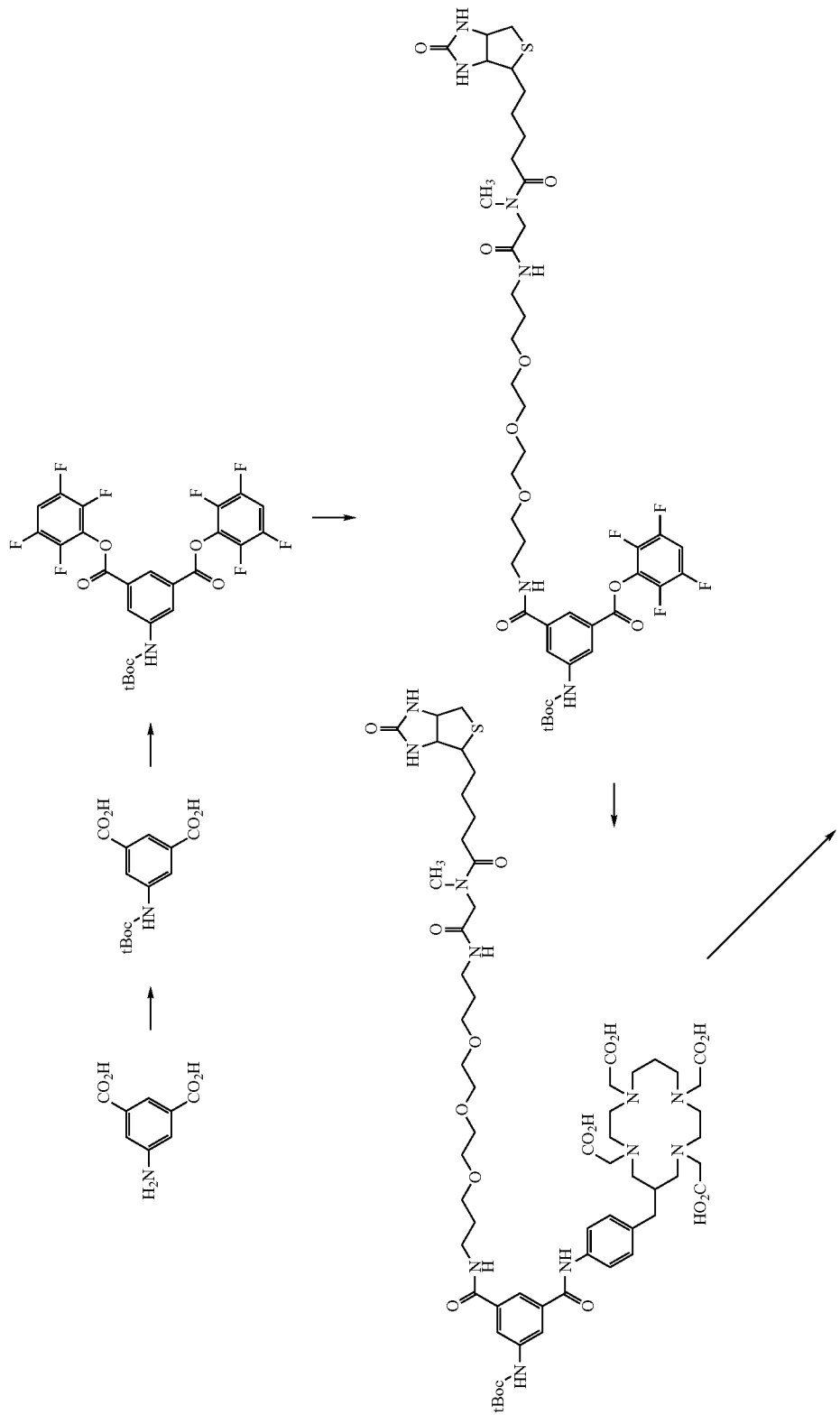

-continued
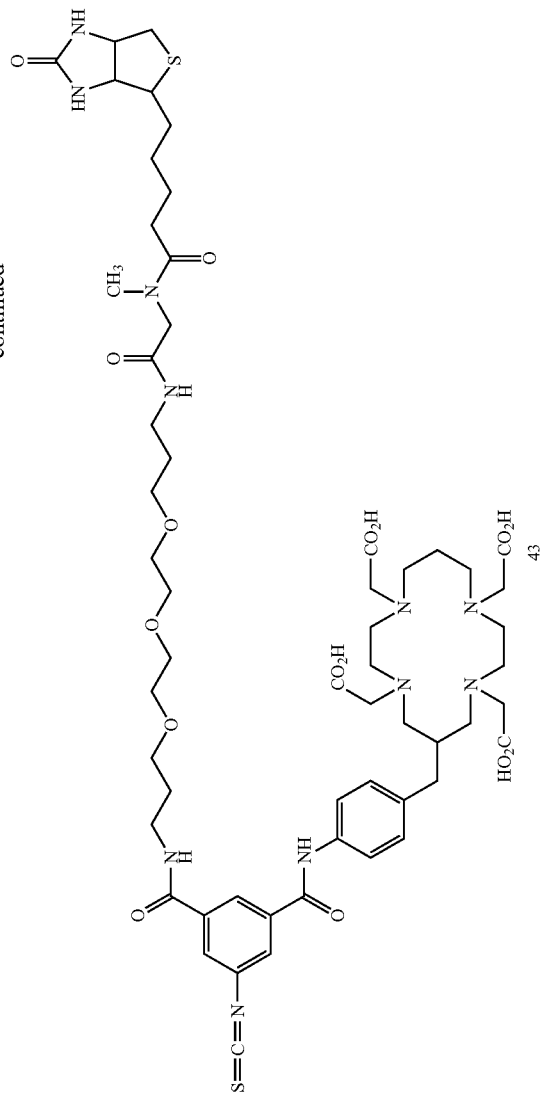

Example 6

Reagent with Homobiotin, Arylstannyl
Radiohalogenation Moiety, and Maleimide

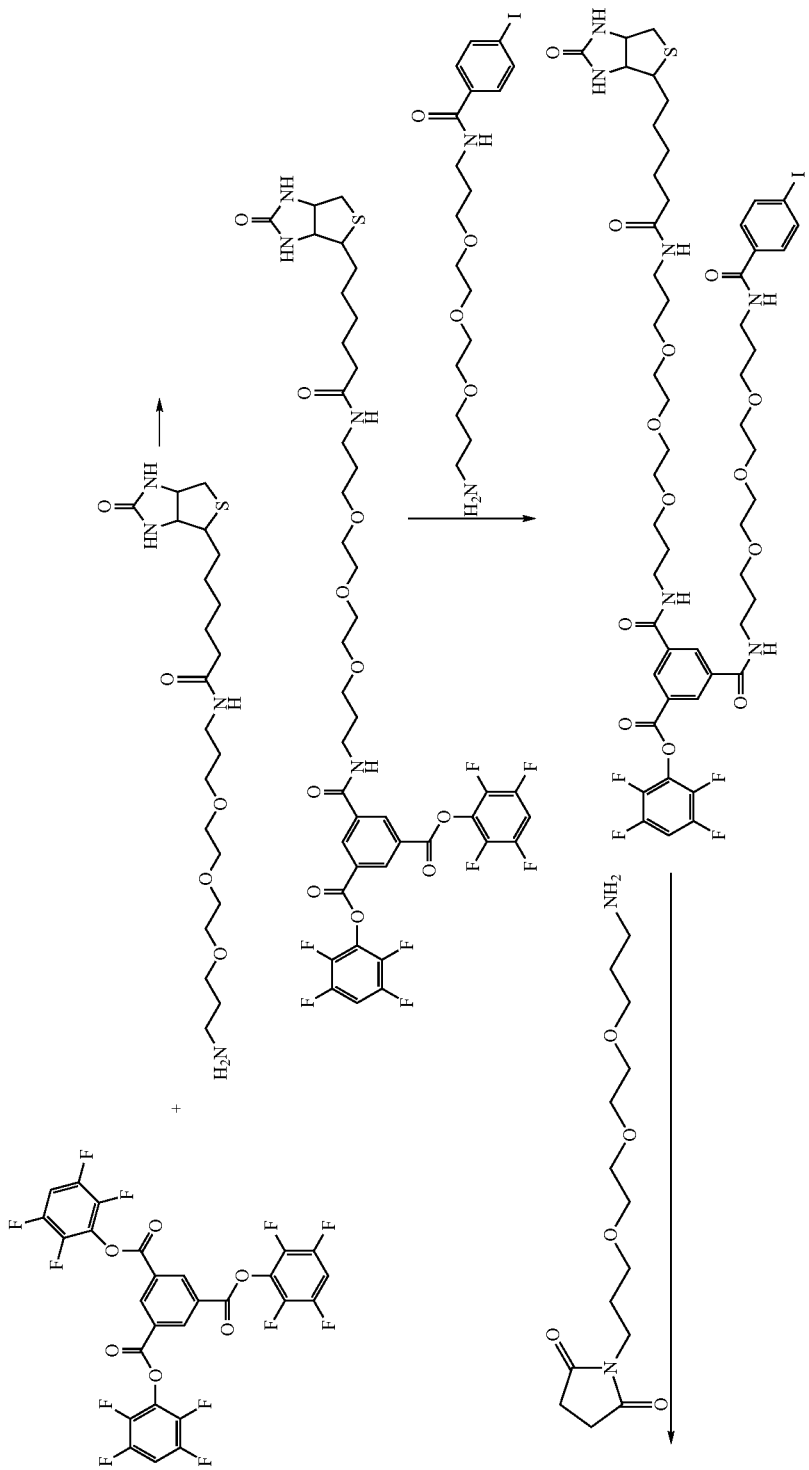

-continued
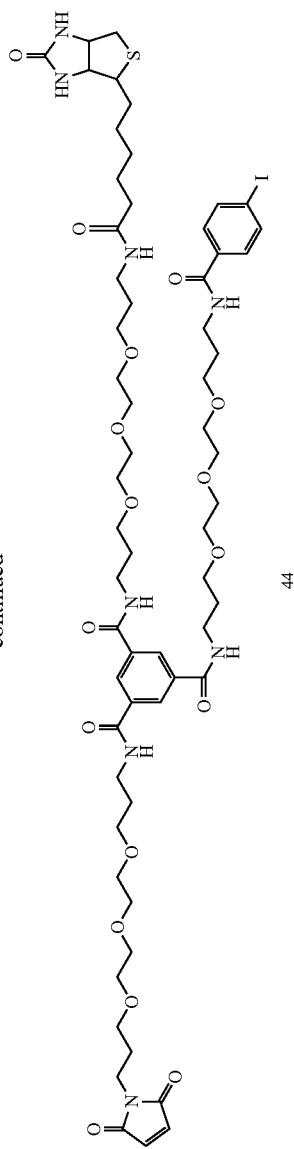
44

Example 7

Reagent with Biotin, Biotinidase Stabilizing Linker, CHX-A"-DTPA Chelate, and Isothiocyanate Conjugation Moiety

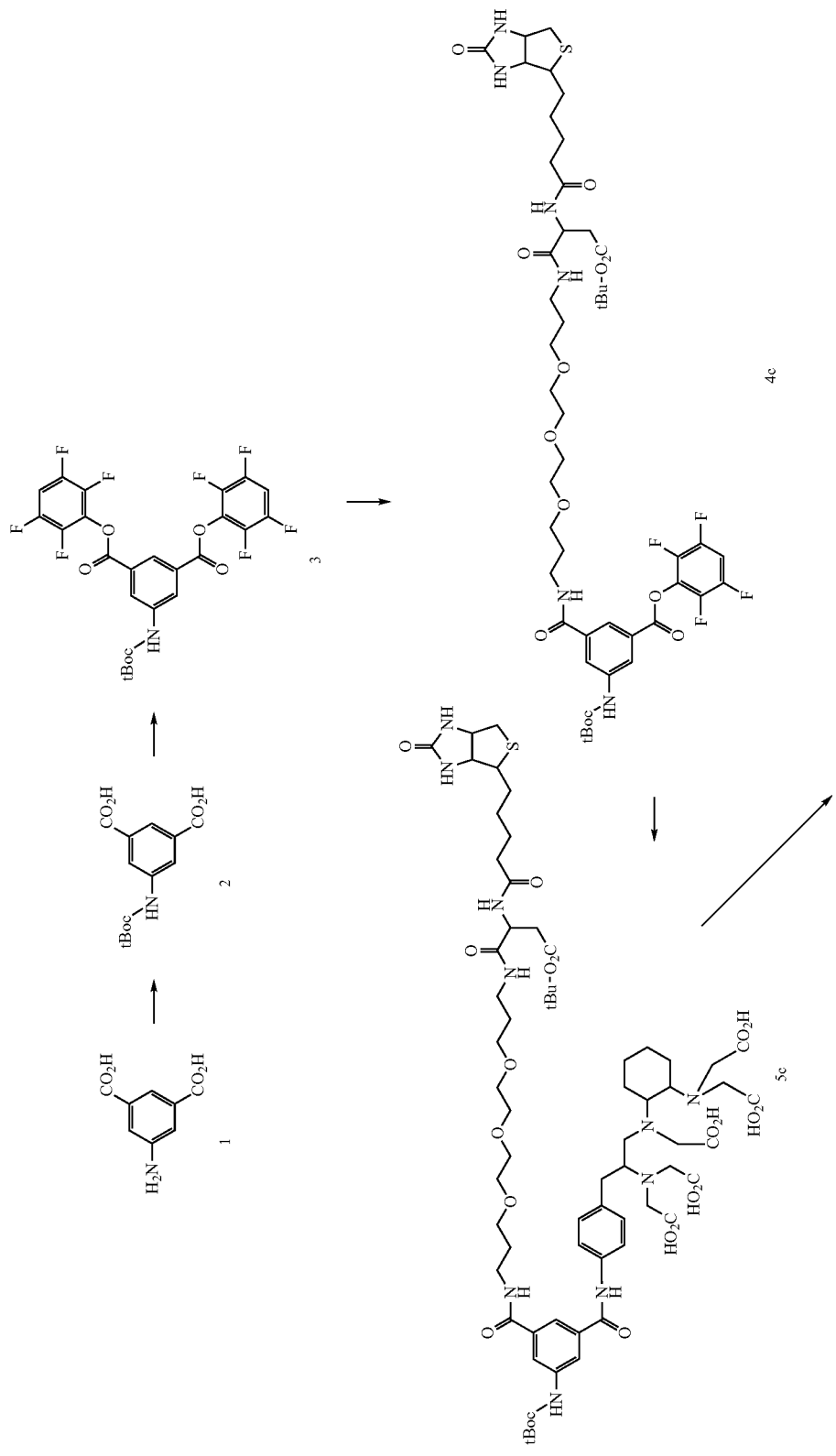

-continued
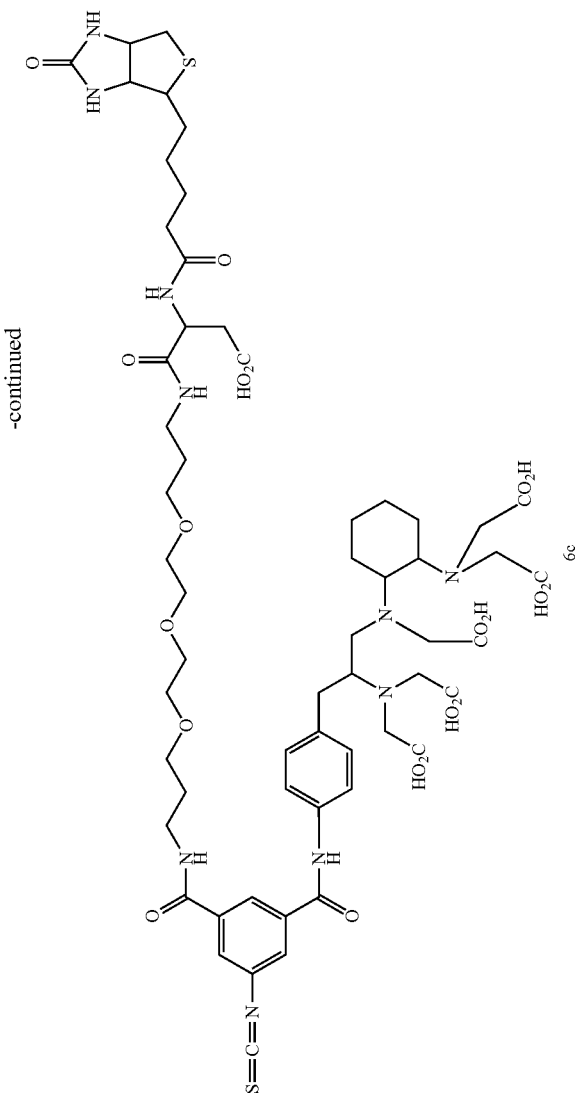

The invention claimed is:

1. A reagent for conjugation to a biomolecule having the formula:

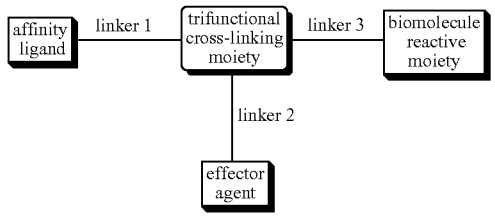

wherein the trifunctional cross-linking moiety is coupled to
a) the affinity ligand via linker 1,
  wherein the affinity ligand is selected from the group consisting of biotin, norbiotin, homobiotin, oxybiotin, iminobiotin, desthiobiotin, diaminobiotin, biotin sulfoxide, and biotin sulfone, and
  wherein linker 1 comprises a carboxylate group or an N-methyl group effective to inhibit biotinidase activity,
b) an effector agent via linker 2, said effector agent exerting its effect on cells, tissues and/or humorous molecules in vivo or ex vivo, and
c) the biomolecule reactive moiety via a linker 3, said moiety being capable of forming a bond between the reagent and the biomolecule.

2. The reagent of claim 1, wherein the trifunctional cross-linking moiety is selected from the group consisting of triaminobenzene, tricarboxybenzene, dicarboxyaniline and diaminobenzoic acid.

3. The reagent of claim 1, wherein linker 1 comprises an ionizable group selected from the group consisting of a carboxylate, a sulfonate, and an ammonium group.

4. The reagent of claim 1, wherein the effector agent is selected from the group consisting of synthetic or natural occurring toxins, enzymes, hormones, immunosuppressive agents, immunostimulating agents, radionuclide binding/bonding moieties, radiosensitizers, enhancers for X-ray or MRI or ultrasound, and photoactive compounds.

5. The reagent of claim 1, wherein the effector agent is a radionuclide binding/bonding moiety selected from the group consisting of amino-carboxy derivatives, cyclic amines, $N_2S_2$, and $N_3S$ chelates.

6. The reagent of claim 1, wherein the effector agent is selected from the group consisting of aryl halides and vinyl halides.

7. The reagent of claim 1 further comprising a positron imaging radionuclide, a therapeutic radionuclide, or a gamma imaging radionuclide.

8. The reagent of claim 1, wherein the effector agent is a photoactive compound.

9. The reagent of claim 1, wherein linker 2 provides a spacer length of 1-25 atoms.

10. The reagent of claim 1, wherein the biomolecule reactive moiety is selected from the group consisting of activated esters, aryl and alkyl imidates, alkyl and aryl isocyanates, alkyl and aryl isothiocyanates, maleimides, and alpha-haloamides, alkyl and aryl hydrazines, and alkyl and aryl hydroxylamines.

11. The reagent of claim 1, wherein linker 3 provides a spacer of a length of 1-25 atoms.

12. The reagent of claim 1 selected from the group consisting of:

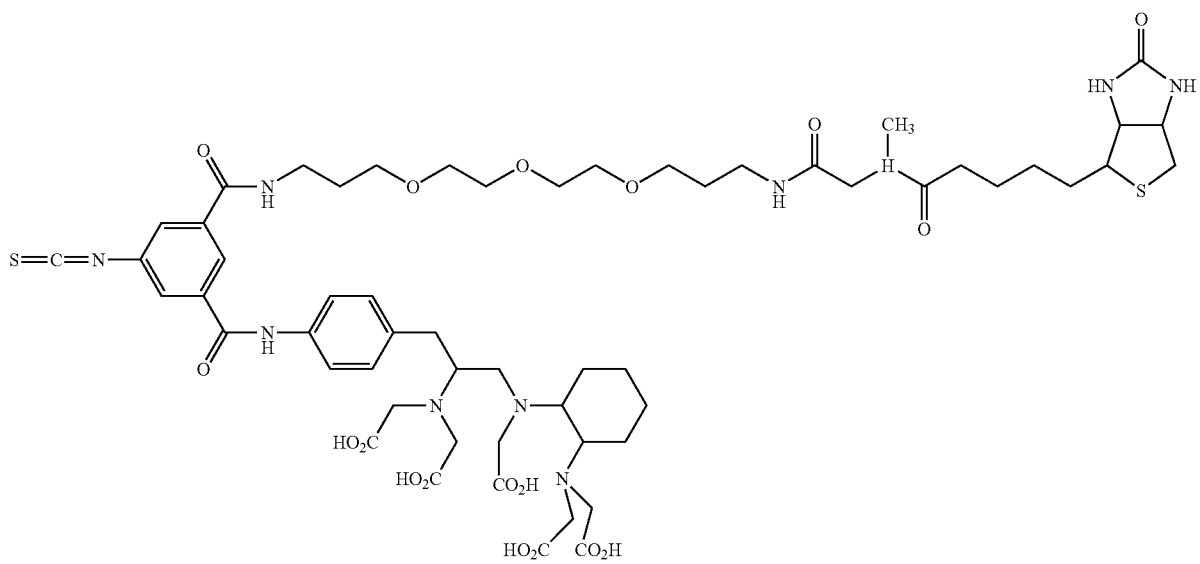

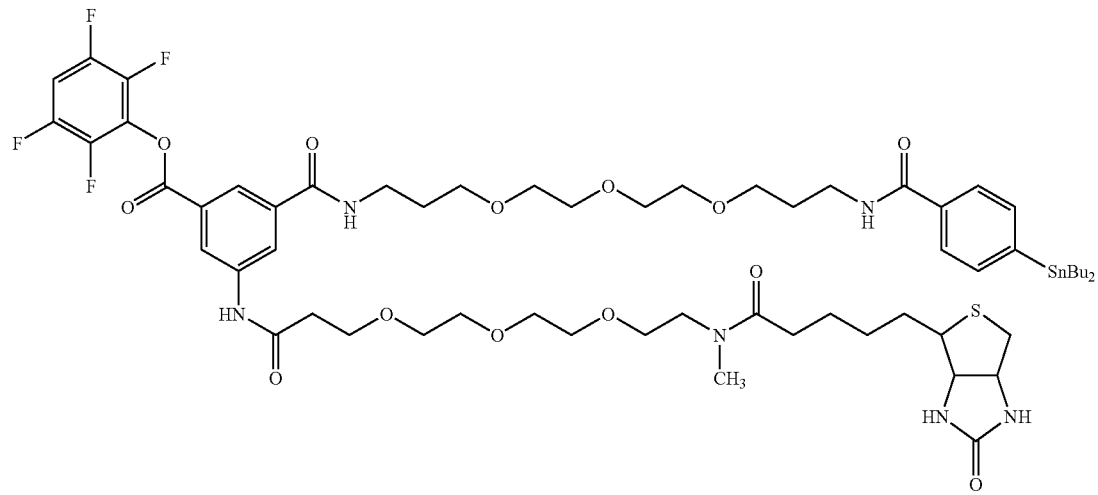
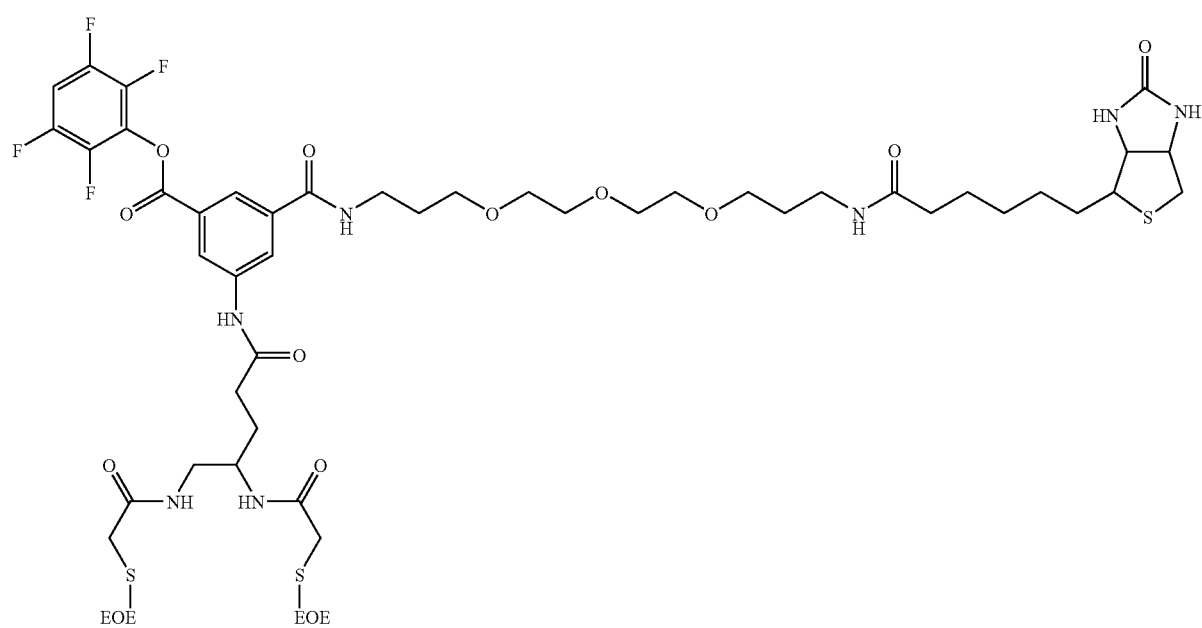

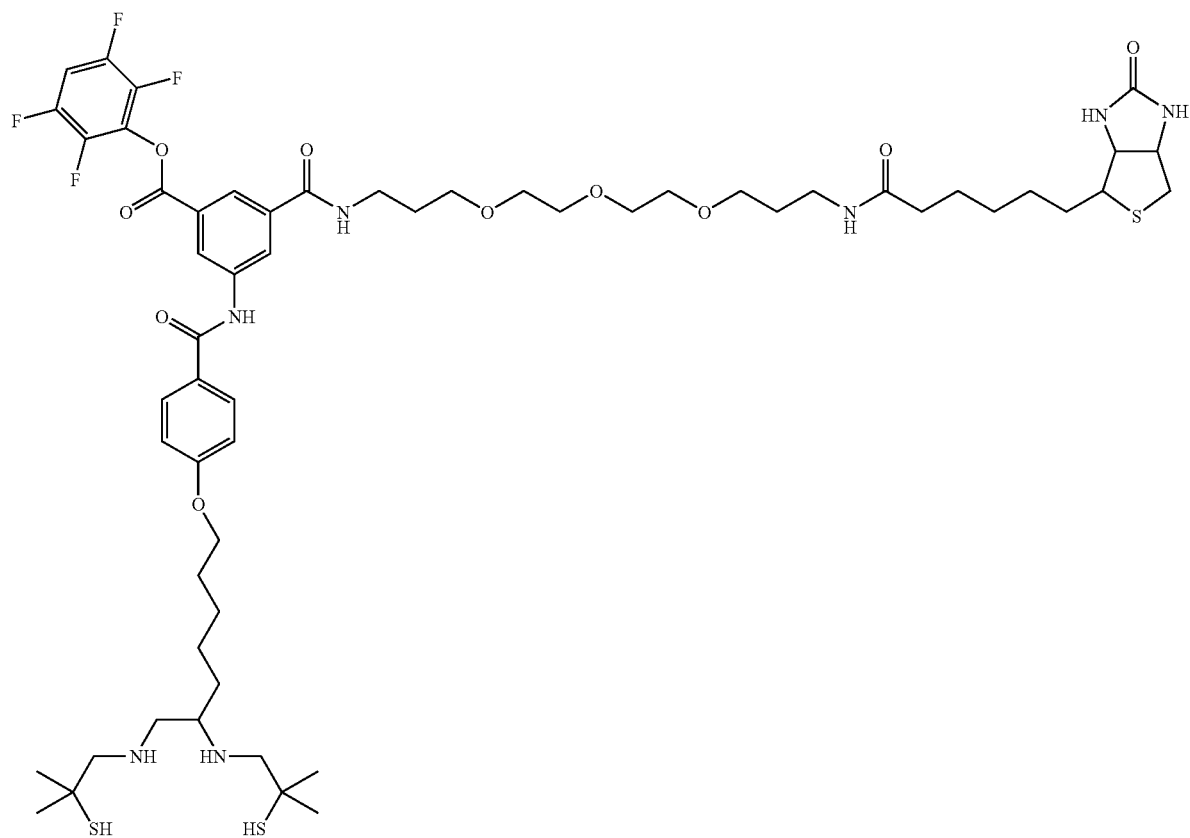
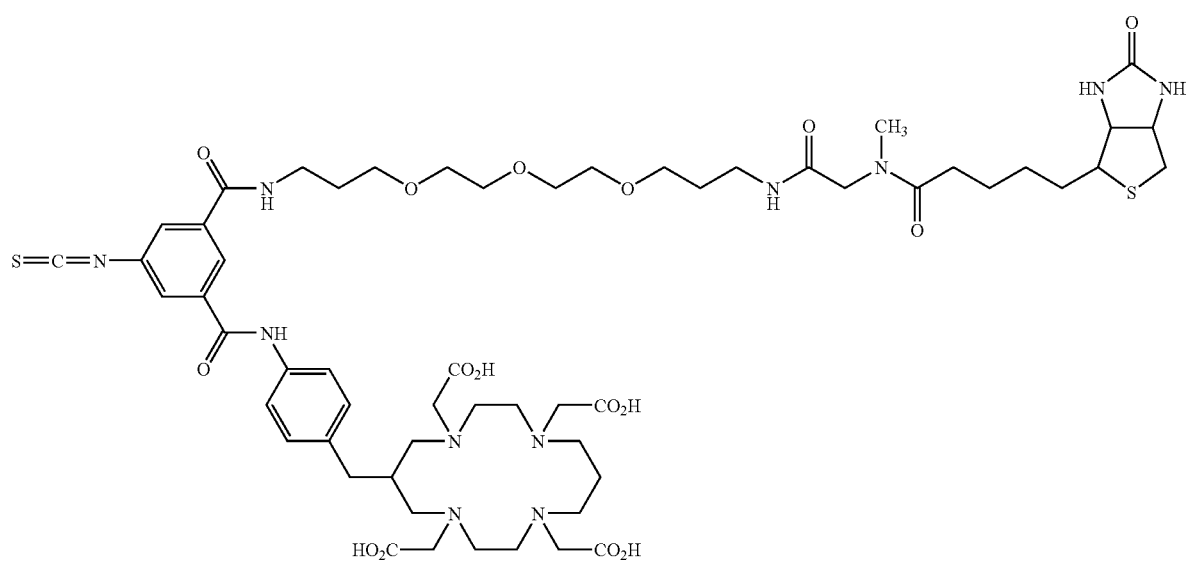

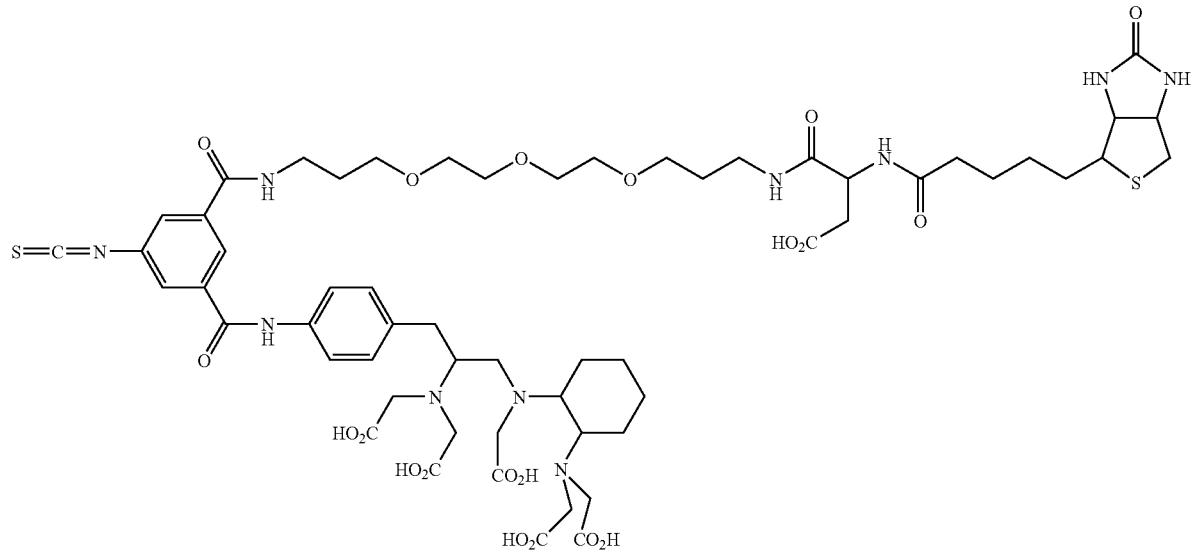

45

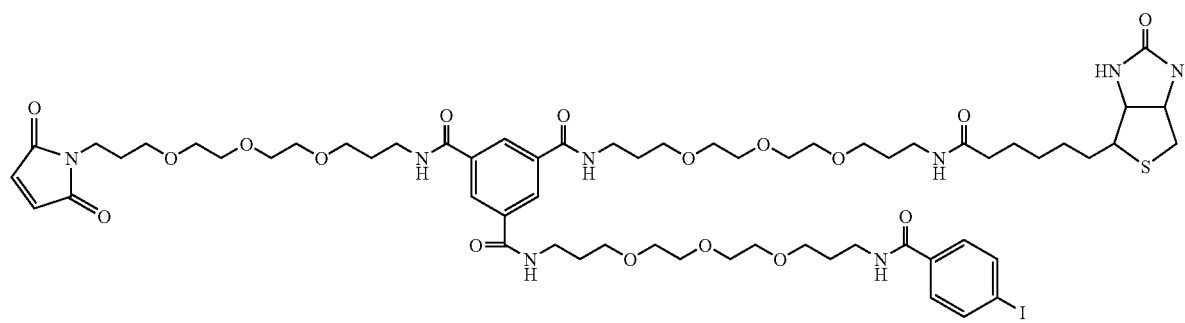

44

13. The reagent of claim 1, wherein the biomolecule is a protein or a peptide.

14. The reagent of claim 1, wherein the biomolecule is a monoclonal antibody.

15. The reagent of claim 1, wherein the biomolecule is a tumor binding monoclonal antibody.

16. The reagent of claim 1, wherein the effector agent is an EDTA derivative, a DTPA derivative, or a cyclic amine.

17. The reagent of claim 1, wherein the effector agent is selected from the group consisting of Me-DTPA, CITC-DTPA, and cyclohexyl-DTPA.

18. The reagent of claim 1, wherein the effector agent is selected from the group consisting of NOTA, DOTA, and TETA.

19. The reagent of claim 7, wherein the positron imaging radionuclide is selected from the group consisting of F-18, Br-75, Br-76, and I-124.

20. The reagent of claim 7, wherein the therapeutic radionuclide is selected from the group consisting of Y-90, I-131, In-114m, Re-186, Re-188, Cu-67, Sm-157, Lu-177, Bi-212, Bi-213, At-211, and Ra-223.

21. The reagent of claim 7, wherein the gamma imaging radionuclide is selected from the group consisting of Tc-99m, In-111, and I-123.

22. The reagent of claim 1, wherein the effector agent is a chromophore, a fluorophore, or a photodynamic therapeutic agent.

23. The reagent of claim 1, wherein linker 2 provides a spacer length of 6-18 atoms.

24. The reagent of claim 1, wherein linker 3 provides a spacer of a length of 6-18 atoms.

25. The reagent of claim 1, wherein the biomolecule reactive moiety is selected from the group consisting of N-hydroxysuccinimide esters, sulfo-N-hydroxysuccinimide esters, and phenolic esters.

* * * * *